(12) United States Patent
Oppert et al.

(10) Patent No.: US 8,354,371 B2
(45) Date of Patent: Jan. 15, 2013

(54) CADHERIN RECEPTOR PEPTIDE FOR POTENTIATING BT BIOPESTICIDES

(75) Inventors: Brenda S. Oppert, Manhattan, KS (US); Juan Luis Jurat-Fuentes, Knoxville, TN (US); Jeffrey A. Fabrick, Maricopa, AZ (US); Cristopher Oppert, Knoxville, TN (US)

(73) Assignees: The United States of America, as represented by the Secretary of Agriculture, Washington, DC (US); The University of Tennesse Research Foundation, Knoxville, TN (US)

( * ) Notice: Subject to any disclaimer, the term of this patent is extended or adjusted under 35 U.S.C. 154(b) by 972 days.

(21) Appl. No.: 12/272,903

(22) Filed: Nov. 18, 2008

(65) Prior Publication Data

US 2009/0175974 A1    Jul. 9, 2009

Related U.S. Application Data

(60) Provisional application No. 60/988,919, filed on Nov. 19, 2007.

(51) Int. Cl.
*A01N 63/02*    (2006.01)
(52) U.S. Cl. ............ 514/1.1; 424/780; 435/32; 530/350
(58) Field of Classification Search ........................ None
See application file for complete search history.

(56) References Cited

U.S. PATENT DOCUMENTS

2011/0183896 A1*    7/2011    Adang et al. .................. 514/4.5

* cited by examiner

*Primary Examiner* — Christopher R. Tate
*Assistant Examiner* — Roy Teller
(74) *Attorney, Agent, or Firm* — John Fado; Albert Y. Tsui; Lesley Shaw

(57) ABSTRACT

Disclosed is a novel cadherin peptide that enhances the toxicity of Cry proteins. A novel insecticide composition comprising an effective amount of cadherin peptide having SEQ. ID. NO:2 and an effective amount of *Bacillus thuringiensis* Cry protein wherein the cadherin peptide comprises a Cry3Aa toxin binding region from the full-length *T. molitor* cadherin and has synergistic characteristics of a binary toxin potentiating Cry3 and Cry1 toxins against coleopterans and lepidopteran species, respectively.

10 Claims, 13 Drawing Sheets

6X His-tag        V5 epitope       TEV site ↓       rTmCad1 1,322

MHHHHHHGKPIPNPLLGLDSTENLYFQGIDPFTEHEDTDKDTTSKDKLQYNIDNITPSN

LDLDIKSAFTMNTQSGDITINFEVKDSMEGYFTLDLSVQDEEPENHKADATLKIYIV

TSKNTVVFRFENDQETVSDKAGDIKSVLDEEFQYETKVEAPTGNTTDGTPLTRSPVF

FLNLNTNEPVDATEILKKVTNVDVFQRLKNNFSKVGLVLLSFDSSSETNENLEAILK rTmCad1 1,516

SEQUENCE LISTING

<160> NUMBER OF SEQ ID NOS: 28

<210> SEQ ID NO 1
<211> LENGTH: 1161
<212> TYPE: DNA
<213> ORGANISM: Tenebrio molitor

<400> SEQUENCE: 1

```
cgactgggag cacgaggaca ctgacatgac tattcaggta gtagaccaga acgacgaatc      60
tccagtgttt gaccaaacgg agtatttcac caccgtctta gccggcacat ctatgtcaac     120
aaaagtgacg acagtttcgg ccactgacaa ggatacaact agtaaggaca gttgcaata     180
caacattgat aacattactc catctaacct cgacctggac ataaaatctg ctttaccat    240
gaatacgcaa tccggagata ttacaattaa ttttgaagtc aaagacagca tggagggtta     300
tttcacgtta gatcttagtg tccaggatga agagccggaa aatcacaaag ctgatgccac     360
tctaaaaatt tatattgtta ctagtaaaaa cactgtagtg tttagatttg aaaatgacca     420
agagaccgtt agtgacaaag ctggagatat taaaagtgta ctggatgaag aatttcaata     480
tgaaactaaa gtcgaagctc aacaggaaa cacgacagac ggtacacctc ttacaaggtc     540
accggttttc ttcctgaact tgaacacaaa tgaacctgtg gatgcaactg agatacttaa     600
gaaagtcacc aacgttgacg tgttccaaag attaaaaaat aactttcga aagttggtct     660
ggtcttattg agtttgatt ccagttccga aaccaacgaa aacttggaag caatttgaa     720
agcgtggttg atcggtgttt cggtagttct cggagcactg tgtctcattc ttttgattgc     780
gtttatactg aaaacgagag ctttgaatca acgtatcaag aagctgtcca gtaccaaatt     840
ttcgggtcgc aagagtcggg gattgaatag gcaaggagtg gcggccccca caaccaacaa     900
acacgcccta gaaggatcaa atccagtgtc aataacgaag tcgaccccga aggacattga     960
taggacgagc gtcacgagcg gcgattcaga tctaatagga gtggaagatg acgagaagtt    1020
tgactttagt tacccaacta aagatgatca gtttgaataa aaaccaaatt atttttat    1080
atttattaag tttaattatg tatataaatt ctactaagtg taaatatacg tacatatttt    1140
ttaaaaaa aaaaaaaaa a                                                    1161
```

<210> SEQ ID NO 2
<211> LENGTH: 205
<212> TYPE: PRT
<213> ORGANISM: Tenebrio molitor

<400> SEQUENCE: 2

```
Gly Ile Asp Pro Phe Thr Glu His Glu Asp Thr Asp Lys Asp Thr Thr
1               5                  10                  15

Ser Lys Asp Lys Leu Gln Tyr Asn Ile Asp Asn Ile Thr Pro Ser Asn
            20                  25                  30

Leu Asp Leu Asp Ile Lys Ser Ala Phe Thr Met Asn Thr Gln Ser Gly
```

|   |   |   |   |   | 35 |   |   |   |   | 40 |   |   |   |   | 45 |   |   |
|---|---|---|---|---|---|---|---|---|---|---|---|---|---|---|---|---|---|

Asp Ile Thr Ile Asn Phe Glu Val Lys Asp Ser Met Glu Gly Tyr Phe
50                      55                      60

Thr Leu Asp Leu Ser Val Gln Asp Glu Glu Pro Glu Asn His Lys Ala
65                      70                      75                      80

Asp Ala Thr Leu Lys Ile Tyr Ile Val Thr Ser Lys Asn Thr Val Val
                85                      90                      95

Phe Arg Phe Glu Asn Asp Gln Glu Thr Val Ser Asp Lys Ala Gly Asp
                100                     105                     110

Ile Lys Ser Val Leu Asp Glu Glu Phe Gln Tyr Glu Thr Lys Val Glu
                115                     120                     125

Ala Pro Thr Gly Asn Thr Thr Asp Gly Thr Pro Leu Thr Arg Ser Pro
130                     135                     140

Val Phe Phe Leu Asn Leu Asn Thr Asn Glu Pro Val Asp Ala Thr Glu
145                     150                     155                     160

Ile Leu Lys Lys Val Thr Asn Val Asp Val Phe Gln Arg Leu Lys Asn
                165                     170                     175

Asn Phe Ser Lys Val Gly Leu Val Leu Leu Ser Phe Asp Ser Ser Ser
                180                     185                     190

Glu Thr Asn Glu Asn Leu Glu Ala Ile Leu Lys Ala Trp
                195                     200                     205

<210> SEQ ID NO 3
<211> LENGTH: 5095
<212> TYPE: DNA
<213> ORGANISM: Tenebrio molitor

<400> SEQUENCE: 3

```
atatcaggtg cgacactgga gtacagcagt tccgtaagtg cgatgtgcga ttatttgtta      60
aaagtttggt gtactgaata taggaataat tgctgatacc tacattcacg aaaatgcgag     120
tcatttttgt gatttttttg ggactactat gtcgcgtttc gtcgttcgag ttcgaagctg     180
tcgaccagga tggggtgaaa ttcggagaca aacgtcaac  agctcaacaa atagaagtag     240
acgagaataa cgatggcggt agagttccaa tagtttcgat aaccggagtg ggggacacac     300
tttcgatgac cggaatgacg agcaactttg acttgctaga cgccgaacta aaaacagatg     360
acaacgtgaa ctaccagctc attgtcaact tgctggatta cgaatcctta gattcaggcg     420
gggacagcgt gcttgtggcc atcaccgaag tgtcaactcc taacacaaga cagccattgc     480
aagtaataat caagaacttg gacgacgaac atccgacgct gacagtttca aactgtattt     540
tggaagaaga aactgtcatc gacgtgaaca attcaccgtg cagttttaca atcagtgatc     600
cggacggttt tttggatacg atggactttt cgaacattgt gggctcgaag ggcgaagctg     660
acaaattcgc atttgcttat aagacgcagc cagcggcgac ggatcgagaa agcgaaattt     720
atttggtgtt gaaagatggg caaaaactgg attacgagac aacaacactg ttcactttta     780
acgtagaagc acaggataac gcccatcatc cgaccacgcc agcgagtgtt ccgatcatag     840
tacaggtgca agacatgcca gaccaaccgc cagtgtggga tgcagctttt cgctcggcta     900
ttacaatacc agaaaagaac gagacgacaa tacaactgtc tgcaaaagat ggagactatg     960
gaattaacaa caacataaaa tataccgtcg aagacgagaa caacttcgct acggtggatg    1020
cctctggtct aattaccgtc agtccaatta acagagatga gggcttcgat caagtcactt    1080
taactgtgac tgcaattgaa gtggaacagc cagactcgac aacagttggc accatactgc    1140
tgatccttga agacattgat gacagcatac cagaaatcag cgtacttgat tcaaccgaga    1200
```

```
agaagattga aatcactatc gatgaaggtg cttctgacgt gccagtcgac atcgtcgtca   1260
ccgatttgga tctgggggca aatgccatct acaacgtcac actagaagca gaaaatgaag   1320 acttttttgtc agcttttaat ataataccag gaaaggggta cgagcaaacg tcacttacgt   1380
taagcatcat cgactccaaa ttgctcaatt atgaaactgc cgattggatc cacattgcaa   1440
tgacgttgca cactcaagga actgacactc caacaaacga agactttta ccaattacaa   1500 tcaacctaaa tgatatcaac gatgagtctc ctatgatatt ccgacgaatg aggtacagtg   1560
tgaggtctca aaatgtaggg gctggatata acctgaccag cataaaagca accgacctcg   1620
atcaggaaga tatagacaat ggattaaagc atgaaatatt gggggcgatg ggaaatacca   1680
tattacagat cgaagatctt ggcggggacg tgaccacaaa aatagacaag gctttcgact   1740
acgaaaaaca gaacgaaatt tacgttcaga ttagagcagt ggatgcagga ggacatccag   1800
cttccactca gttgactatc aatgtaattg acgtgaatga cgaaaatcct agattggttg   1860
tgtcatcgac aattgctgta gaggaaaatc agcctgacaa ctaccctctt gaaacaaata   1920
ttgcggcatc cgacgaagac agcgacgcag atttggagtt ctcgatagat tggagcaaat   1980
cttacgcaac taaaaactcc caaagaataa aagattttga aactatcat tgcatcaacg   2040 tggagacagt tccaggggat gatcttcaca cagccacagc taaactaagc ctaaaggaaa   2100
cacaacctgg caacactcct gactatgaga catttgacac gttatacatt caattaacag   2160
tgaccgacaa aaatacaacg gaaggagaag gcaccgactc agctctgatt gttatcaaca   2220
tccaagatgt gaacgacaac aagccgatat ttgctgacaa cactgcagaa ctaaaaagag   2280
aagttactga aaatactaaa gatggaatca tcatcacaac tgtgacagct actgacgctg   2340
acatggacaa caatgtaaca tacgctatta agagtgctga tgagaacact cccgactggg   2400
ttgcgatcga tgcgtttggg agtgtgtatg tcaagttaga aggtgatgac cagatcgatt   2460
gtgacgatcc taaacgagac gttttagtat atacagtaac cgcaagtgat ggagatccag   2520
accatgacaa ttcaatcaat ataaccattg cgataaccga ccagaacgac aatgttcctg   2580
tcatggagga ccaaagcgaa gaaatagacg aagacaacca gcttgatccg gacgacaccc   2640
tcaacggacg tactatactt aatctaacat atagtgatgc cgatagagac gaaccataca   2700
atgtggtgag gtgtacttt gccacttcca cgagcgacga ggtcatcgac aggttcacaa   2760
ttacagacaa cactgtggtg atttcgttgg cagctgagc cactttagac agagaagaac   2820
attccgagtt tcaatttggg cttagctgca cagatgatcc ccaacatcaa ggaccagtct   2880
caaacgccat ttctccacct ccaagaatca caataaaact gaacgacatc aacgacaaca   2940
aacctcaagt gacgaccact gaaataacgg gaattaccga aaacacctca aagggaccgc   3000
tgggccaaaa acttcagggg aaagatgacg atgaaggtga caagggtctg ataaccttcg   3060
ccataaataa agtcctgaga tatatttctg atgatgacga cgcacctaca gacgtcaccg   3120
accagtttga cattacagac gaagaggatg gtaaaagcgc cactttgagc ctattaggag   3180
acaatttgag cggcctgtgg ggtcgtctgg aagcgacgat tgatgtaact gacaagggga   3240
cgcctgcact aaacggtcaa aacgtcgtca aaattgatgt cgccaagtac aatttcaaag   3300
agcctatatt cgacttcccc aaacagggag attcgtacta cttcaagacg atacaagata   3360
aagacgcccc gctcaaactc tggaacggag gcaatatgga caacgtgaaa gcgaacgatc   3420
aacaaggcaa caaatacagt ataaaatttg acgttgttga ggatagtagc gaccagaatt   3480
tgtttaaagt tgcctatctc ggaaattcgc aaggacagct tcagctaact aatgccgact   3540
ttgtgccgaa accttacacg gtgactctgc gggcatcttt ggacgtcgac aacagtcccg   3600
```

-continued

```
ccaatggaga ggcatcttac gaagtgaatt gtaccataaa tatcaatttc ttcgatagtg    3660
acagcaccga tccggtattt gagcatcaca gtgataccac tctattcact gaaaattccg    3720
acacggaatc gtaccaagtt gaaaacgcaa cgtatcccga tatcgacctt ccagatttgg    3780
cagtctatta tctgataaga gagggtgaca caacgctttt taagattgac caatcaacag    3840
gaacaatcac ccttaaacaa ccgctcgact acgaaacaca atcttcgtac gaagtgctga    3900
ttcagtcatc taacgctgac aagcttaact tggatgcatt agaagaaacg aaatttgcgt    3960
tgactattca ggtagtagac cagaacgacg aatctccagt gtttgaccaa acggagtatt    4020
tcaccaccgt cttagccggc acatctatgt caacaaaagt gacgacagtt tcggccactg    4080
acaaggatac aactagtaag gacaagttgc aatacaacat tgataacatt actccatcta    4140
acctcgacct ggacataaaa tctgctttta ccatgaatac gcaatccgga gatattacaa    4200
ttaattttga agtcaaagac agcatggagg ttatttcac gttagatctt agtgtccagg     4260
atgaagagcc ggaaaatcac aaagctgatg ccactctaaa aatttatatt gttactagta    4320
aaaacactgt agtgtttaga tttgaaaatg accaagagac cgttagtgac aaagctggag    4380
atattaaaag tgtactggat gaagaatttc aatatgaaac taaagtcgaa gctccaacag    4440
gaaacacgac agacggtaca cctcttacaa ggtcaccggt tttcttcctg aacttgaaca    4500
caaatgaacc tgtggatgca actgagatac ttaagaaagt caccaacgtt gacgtgttcc    4560
aaagattaaa aaataacttt tcgaaagttg gtctggtctt attgagtttt gattccagtt    4620
ccgaaaccaa cgaaaacttg gaagcaattt tgaaagcgtg gttgatcggt gtttcggtag    4680
ttctcggagc actgtgtctc attcttttga ttgcgtttat actgaaaacg agagctttga    4740
atcaacgtat caagaagctg tccagtacca aattttcggg tcgcaagagt cggggattga    4800
ataggcaagg agtggcggcc cccacaacca acaaacacgc cctagaagga tcaaatccag    4860
tgtcaataac gaagtcgacc ccgaaggaca ttgataggac gagcgtcacg agcggcgatt    4920
cagatctaat aggagtggaa gatgacgaga agtttgactt tagttaccca actaaagatg    4980
atcagtttga ataaaaacca aattatttt tattatttat taagtttaat tatgtatata      5040
aattctacta agtgtaaata tacgtacata ttttttaaa aaaaaaaaa aaaaa            5095
```

<210> SEQ ID NO 4
<211> LENGTH: 1626
<212> TYPE: PRT
<213> ORGANISM: Tenebrio molitor

<400> SEQUENCE: 4

```
Met Arg Val Ile Phe Val Ile Phe Leu Gly Leu Leu Cys Arg Val Ser
1               5                   10                  15

Ser Phe Glu Phe Glu Ala Val Asp Gln Asp Gly Val Lys Phe Gly Asp
            20                  25                  30

Lys Thr Ser Thr Ala Gln Gln Ile Glu Val Asp Glu Asn Asn Asp Gly
        35                  40                  45

Gly Arg Val Pro Ile Val Ser Ile Thr Gly Val Gly Asp Thr Leu Ser
    50                  55                  60

Met Thr Gly Met Thr Ser Asn Phe Asp Leu Leu Asp Ala Glu Leu Lys
65                  70                  75                  80

Thr Asp Asp Asn Val Asn Tyr Gln Leu Ile Val Asn Leu Leu Asp Tyr
                85                  90                  95

Glu Ser Leu Asp Ser Gly Gly Asp Ser Val Leu Val Ala Ile Thr Glu
            100                 105                 110

Val Ser Thr Pro Asn Thr Arg Gln Pro Leu Gln Val Ile Ile Lys Asn
```

```
            115                 120                 125
Leu Asp Asp Glu His Pro Thr Leu Thr Val Ser Asn Cys Ile Leu Glu
130                 135                 140

Glu Glu Thr Val Ile Asp Val Asn Asn Ser Pro Cys Ser Phe Thr Ile
145                 150                 155                 160

Ser Asp Pro Asp Gly Phe Leu Asp Thr Met Asp Phe Ser Asn Ile Val
                    165                 170                 175

Gly Ser Lys Gly Glu Ala Asp Lys Phe Ala Phe Ala Tyr Lys Thr Gln
                    180                 185                 190

Pro Ala Ala Thr Asp Arg Glu Ser Glu Ile Tyr Leu Val Leu Lys Asp
                    195                 200                 205

Gly Gln Lys Leu Asp Tyr Glu Thr Thr Thr Leu Phe Thr Phe Asn Val
210                 215                 220

Glu Ala Gln Asp Asn Ala His His Pro Thr Thr Pro Ala Ser Val Pro
225                 230                 235                 240

Ile Ile Val Gln Val Gln Asp Met Pro Asp Gln Pro Val Trp Asp
                    245                 250                 255

Ala Ala Phe Arg Ser Ala Ile Thr Ile Pro Glu Lys Asn Glu Thr Thr
                    260                 265                 270

Ile Gln Leu Ser Ala Lys Asp Gly Asp Tyr Gly Ile Asn Asn Asn Ile
                    275                 280                 285

Lys Tyr Thr Val Glu Asp Glu Asn Asn Phe Ala Thr Val Asp Ala Ser
                    290                 295                 300

Gly Leu Ile Thr Val Ser Pro Ile Asn Arg Asp Glu Gly Phe Asp Gln
305                 310                 315                 320

Val Thr Leu Thr Val Thr Ala Ile Glu Val Glu Gln Pro Asp Ser Thr
                    325                 330                 335

Thr Val Gly Thr Ile Leu Leu Ile Leu Glu Asp Ile Asp Asp Ser Ile
                    340                 345                 350

Pro Glu Ile Ser Val Leu Asp Ser Thr Glu Lys Lys Ile Glu Ile Thr
                    355                 360                 365

Ile Asp Glu Gly Ala Ser Asp Val Pro Val Asp Ile Val Thr Asp
370                 375                 380

Leu Asp Leu Gly Ala Asn Ala Ile Tyr Asn Val Thr Leu Glu Ala Glu
385                 390                 395                 400

Asn Glu Asp Phe Leu Ser Ala Phe Asn Ile Ile Pro Gly Lys Gly Tyr
                    405                 410                 415

Glu Gln Thr Ser Leu Thr Leu Ser Ile Ile Asp Ser Lys Leu Leu Asn
                    420                 425                 430

Tyr Glu Thr Ala Asp Trp Ile His Ile Ala Met Thr Leu His Thr Gln
                    435                 440                 445

Gly Thr Asp Thr Pro Thr Asn Glu Asp Phe Leu Pro Ile Thr Ile Asn
                    450                 455                 460

Leu Asn Asp Ile Asn Asp Glu Ser Pro Met Ile Phe Arg Arg Met Arg
465                 470                 475                 480

Tyr Ser Val Arg Ser Gln Asn Val Gly Ala Gly Tyr Asn Leu Thr Ser
                    485                 490                 495

Ile Lys Ala Thr Asp Leu Asp Gln Glu Asp Ile Asp Asn Gly Leu Lys
                    500                 505                 510

His Glu Ile Leu Gly Ala Met Gly Asn Thr Ile Leu Gln Ile Glu Asp
                    515                 520                 525

Leu Gly Gly Asp Val Thr Thr Lys Ile Asp Lys Ala Phe Asp Tyr Glu
530                 535                 540
```

-continued

```
Lys Gln Asn Glu Ile Tyr Val Gln Ile Arg Ala Val Asp Ala Gly Gly
545                 550                 555                 560

His Pro Ala Ser Thr Gln Leu Thr Ile Asn Val Ile Asp Val Asn Asp
                565                 570                 575

Glu Asn Pro Arg Leu Val Val Ser Ser Thr Ile Ala Val Glu Glu Asn
            580                 585                 590

Gln Pro Asp Asn Tyr Pro Leu Glu Thr Asn Ile Ala Ala Ser Asp Glu
        595                 600                 605

Asp Ser Asp Ala Asp Leu Glu Phe Ser Ile Asp Trp Ser Lys Ser Tyr
610                 615                 620

Ala Thr Lys Asn Ser Gln Arg Ile Lys Asp Phe Glu Asn Tyr His Cys
625                 630                 635                 640

Ile Asn Val Glu Thr Val Pro Gly Asp Leu His Thr Ala Thr Ala
                645                 650                 655

Lys Leu Ser Leu Lys Glu Thr Gln Pro Gly Asn Thr Pro Asp Tyr Glu
            660                 665                 670

Thr Phe Asp Thr Leu Tyr Ile Gln Leu Thr Val Thr Asp Lys Asn Thr
        675                 680                 685

Thr Glu Gly Gly Thr Asp Ser Ala Leu Ile Val Ile Asn Ile Gln
690                 695                 700

Asp Val Asn Asp Asn Lys Pro Ile Phe Ala Asp Asn Thr Ala Glu Leu
705                 710                 715                 720

Lys Arg Glu Val Thr Glu Asn Thr Lys Asp Gly Ile Ile Ile Thr Thr
                725                 730                 735

Val Thr Ala Thr Asp Ala Asp Met Asp Asn Asn Val Thr Tyr Ala Ile
            740                 745                 750

Lys Ser Ala Asp Glu Asn Thr Pro Asp Trp Val Ala Ile Asp Ala Phe
        755                 760                 765

Gly Ser Val Tyr Val Lys Leu Glu Gly Asp Asp Gln Ile Asp Cys Asp
770                 775                 780

Asp Pro Lys Arg Asp Val Leu Val Tyr Thr Val Thr Ala Ser Asp Gly
785                 790                 795                 800

Asp Pro Asp His Asp Asn Ser Ile Asn Ile Thr Ile Ala Ile Thr Asp
                805                 810                 815

Gln Asn Asp Asn Val Pro Val Met Glu Asp Gln Ser Glu Glu Ile Asp
            820                 825                 830

Glu Asp Asn Gln Leu Asp Pro Asp Asp Thr Leu Asn Gly Arg Thr Ile
        835                 840                 845

Leu Asn Leu Thr Tyr Ser Asp Ala Asp Arg Asp Glu Pro Tyr Asn Val
850                 855                 860

Val Arg Cys Thr Phe Ala Thr Ser Thr Ser Asp Glu Val Ile Asp Arg
865                 870                 875                 880

Phe Thr Ile Thr Asp Asn Thr Val Val Ile Ser Leu Ala Ala Gly Ala
                885                 890                 895

Thr Leu Asp Arg Glu Glu His Ser Glu Phe Gln Phe Gly Leu Ser Cys
            900                 905                 910

Thr Asp Asp Pro Gln His Gln Gly Pro Val Ser Asn Ala Ile Ser Pro
        915                 920                 925

Pro Pro Arg Ile Thr Ile Lys Leu Asn Asp Ile Asn Asp Asn Lys Pro
930                 935                 940

Gln Val Thr Thr Thr Glu Ile Thr Gly Ile Thr Glu Asn Thr Ser Lys
945                 950                 955                 960

Gly Pro Leu Gly Gln Lys Leu Gln Gly Lys Asp Asp Glu Gly Asp
                965                 970                 975
```

```
Lys Gly Leu Ile Thr Phe Ala Ile Asn Lys Val Leu Arg Tyr Ile Ser
            980                 985                 990

Asp Asp Asp Asp Ala Pro Thr Asp  Val Thr Asp Gln Phe  Asp Ile Thr
            995             1000                 1005

Asp Glu  Glu Asp Gly Lys Ser  Ala Thr Leu Ser Leu  Leu Gly Asp
    1010             1015                 1020

Asn Leu  Ser Gly Leu Trp Gly  Arg Leu Glu Ala Thr  Ile Asp Val
    1025             1030                 1035

Thr Asp  Lys Gly Thr Pro Ala  Leu Asn Gly Gln Asn  Val Val Lys
    1040             1045                 1050

Ile Asp  Val Ala Lys Tyr Asn  Phe Lys Glu Pro Ile  Phe Asp Phe
    1055             1060                 1065

Pro Lys  Gln Gly Asp Ser Tyr  Tyr Phe Lys Thr Ile  Gln Asp Lys
    1070             1075                 1080

Asp Ala  Pro Leu Lys Leu Trp  Asn Gly Gly Asn Met  Asp Asn Val
    1085             1090                 1095

Lys Ala  Asn Asp Gln Gln Gly  Asn Lys Tyr Ser Ile  Lys Phe Asp
    1100             1105                 1110

Val Val  Glu Asp Ser Ser Asp  Gln Asn Leu Phe Lys  Val Ala Tyr
    1115             1120                 1125

Leu Gly  Asn Ser Gln Gly Gln  Leu Gln Leu Thr Asn  Ala Asp Phe
    1130             1135                 1140

Val Pro  Lys Pro Tyr Thr Val  Thr Leu Arg Ala Ser  Leu Asp Val
    1145             1150                 1155

Asp Asn  Ser Pro Ala Asn Gly  Glu Ala Ser Tyr Glu  Val Asn Cys
    1160             1165                 1170

Thr Ile  Asn Ile Asn Phe Phe  Asp Ser Asp Ser Thr  Asp Pro Val
    1175             1180                 1185

Phe Glu  His His Ser Asp Thr  Thr Leu Phe Thr Glu  Asn Ser Asp
    1190             1195                 1200

Thr Glu  Ser Tyr Gln Val Glu  Asn Ala Thr Tyr Pro  Asp Ile Asp
    1205             1210                 1215

Leu Pro  Asp Leu Ala Val Tyr  Tyr Leu Ile Arg Glu  Gly Asp Thr
    1220             1225                 1230

Thr Leu  Phe Lys Ile Asp Gln  Ser Thr Gly Thr Ile  Thr Leu Lys
    1235             1240                 1245

Gln Pro  Leu Asp Tyr Glu Thr  Gln Ser Ser Tyr Glu  Val Leu Ile
    1250             1255                 1260

Gln Ser  Ser Asn Ala Asp Lys  Leu Asn Leu Asp Ala  Leu Glu Glu
    1265             1270                 1275

Thr Lys  Phe Ala Leu Thr Ile  Gln Val Val Asp Gln  Asn Asp Glu
    1280             1285                 1290

Ser Pro  Val Phe Asp Gln Thr  Glu Tyr Phe Thr Thr  Val Leu Ala
    1295             1300                 1305

Gly Thr  Ser Met Ser Thr Lys  Val Thr Thr Val Ser  Ala Thr Asp
    1310             1315                 1320

Lys Asp  Thr Thr Ser Lys Asp  Lys Leu Gln Tyr Asn  Ile Asp Asn
    1325             1330                 1335

Ile Thr  Pro Ser Asn Leu Asp  Leu Asp Ile Lys Ser  Ala Phe Thr
    1340             1345                 1350

Met Asn  Thr Gln Ser Gly Asp  Ile Thr Ile Asn Phe  Glu Val Lys
    1355             1360                 1365

Asp Ser  Met Glu Gly Tyr Phe  Thr Leu Asp Leu Ser  Val Gln Asp
```

```
                        1370                1375                1380

Glu Glu Pro Glu Asn His Lys Ala Asp Ala Thr Leu Lys Ile Tyr
    1385                1390                1395

Ile Val Thr Ser Lys Asn Thr Val Val Phe Arg Phe Glu Asn Asp
1400                1405                1410

Gln Glu Thr Val Ser Asp Lys Ala Gly Asp Ile Lys Ser Val Leu
    1415                1420                1425

Asp Glu Glu Phe Gln Tyr Glu Thr Lys Val Glu Ala Pro Thr Gly
    1430                1435                1440

Asn Thr Thr Asp Gly Thr Pro Leu Thr Arg Ser Pro Val Phe Phe
    1445                1450                1455

Leu Asn Leu Asn Thr Asn Glu Pro Val Asp Ala Thr Glu Ile Leu
    1460                1465                1470

Lys Lys Val Thr Asn Val Asp Val Phe Gln Arg Leu Lys Asn Asn
    1475                1480                1485

Phe Ser Lys Val Gly Leu Val Leu Leu Ser Phe Asp Ser Ser Ser
    1490                1495                1500

Glu Thr Asn Glu Asn Leu Glu Ala Ile Leu Lys Ala Trp Leu Ile
    1505                1510                1515

Gly Val Ser Val Val Leu Gly Ala Leu Cys Leu Ile Leu Leu Ile
    1520                1525                1530

Ala Phe Ile Leu Lys Thr Arg Ala Leu Asn Gln Arg Ile Lys Lys
    1535                1540                1545

Leu Ser Ser Thr Lys Phe Ser Gly Arg Lys Ser Arg Gly Leu Asn
    1550                1555                1560

Arg Gln Gly Val Ala Ala Pro Thr Thr Asn Lys His Ala Leu Glu
    1565                1570                1575

Gly Ser Asn Pro Val Ser Ile Thr Lys Ser Thr Pro Lys Asp Ile
    1580                1585                1590

Asp Arg Thr Ser Val Thr Ser Gly Asp Ser Asp Leu Ile Gly Val
    1595                1600                1605

Glu Asp Asp Glu Lys Phe Asp Phe Ser Tyr Pro Thr Lys Asp Asp
    1610                1615                1620

Gln Phe Glu
    1625

<210> SEQ ID NO 5
<211> LENGTH: 26
<212> TYPE: DNA
<213> ORGANISM: Tenebrio molitor

<400> SEQUENCE: 5
tgaaagcgtg gttgatcggt gtttcg                                           26

<210> SEQ ID NO 6
<211> LENGTH: 27
<212> TYPE: DNA
<213> ORGANISM: Tenebrio molitor

<400> SEQUENCE: 6
tccagtacca aattcgggtc gcaagag                                          27

<210> SEQ ID NO 7
<211> LENGTH: 28
<212> TYPE: DNA
<213> ORGANISM: Tenebrio molitor

<400> SEQUENCE: 7
```

```
ggcatcagct ttgtgatttt ccggctct                                          28

<210> SEQ ID NO 8
<211> LENGTH: 25
<212> TYPE: DNA
<213> ORGANISM: Tenebrio molitor

<400> SEQUENCE: 8
tgtccaggtc gaggttagat ggagt                                             25

<210> SEQ ID NO 9
<211> LENGTH: 25
<212> TYPE: DNA
<213> ORGANISM: Tenebrio molitor

<400> SEQUENCE: 9
tctccggatt gcgtattcat ggtaa                                             25

<210> SEQ ID NO 10
<211> LENGTH: 30
<212> TYPE: DNA
<213> ORGANISM: Tenebrio molitor

<400> SEQUENCE: 10
tcaaacactg gagattcgtc gttctggtct                                        30

<210> SEQ ID NO 11
<211> LENGTH: 24
<212> TYPE: DNA
<213> ORGANISM: Tenebrio molitor

<400> SEQUENCE: 11
gcttgtcagc gttagatgac tgaa                                              24

<210> SEQ ID NO 12
<211> LENGTH: 20
<212> TYPE: DNA
<213> ORGANISM: Tenebrio molitor

<400> SEQUENCE: 12
gagcggttgt ttaagggtga                                                   20

<210> SEQ ID NO 13
<211> LENGTH: 24
<212> TYPE: DNA
<213> ORGANISM: Tenebrio molitor

<400> SEQUENCE: 13
tgtcaccttc atcgtcatct ttcc                                              24

<210> SEQ ID NO 14
<211> LENGTH: 26
<212> TYPE: DNA
<213> ORGANISM: Tenebrio molitor

<400> SEQUENCE: 14
tcatcgttgc atatcattta ggttga                                            26
```

```
<210> SEQ ID NO 15
<211> LENGTH: 24
<212> TYPE: DNA
<213> ORGANISM: Tenebrio molitor

<400> SEQUENCE: 15
cgacgcagat ttggagttct cgat                                          24

<210> SEQ ID NO 16
<211> LENGTH: 24
<212> TYPE: DNA
<213> ORGANISM: Tenebrio molitor

<400> SEQUENCE: 16
caacccagtc gggagtgttc tcat                                          24

<210> SEQ ID NO 17
<211> LENGTH: 28
<212> TYPE: DNA
<213> ORGANISM: Tenebrio molitor

<400> SEQUENCE: 17
tcaagaactt ggacgacgaa catccgac                                      28

<210> SEQ ID NO 18
<211> LENGTH: 27
<212> TYPE: DNA
<213> ORGANISM: Tenebrio molitor

<400> SEQUENCE: 18
ggcatccacc gtagcgaagt tgttctc                                       27

<210> SEQ ID NO 19
<211> LENGTH: 22
<212> TYPE: DNA
<213> ORGANISM: Tenebrio molitor

<400> SEQUENCE: 19
aatgtcttca aggatcagca gt                                            22

<210> SEQ ID NO 20
<211> LENGTH: 24
<212> TYPE: DNA
<213> ORGANISM: Tenebrio molitor

<400> SEQUENCE: 20
caccgagcac gaggacactg acat                                          24

<210> SEQ ID NO 21
<211> LENGTH: 26
<212> TYPE: DNA
<213> ORGANISM: Tenebrio molitor

<400> SEQUENCE: 21
ctaccacgct ttcaaaattg cttcca                                        26

<210> SEQ ID NO 22
<211> LENGTH: 27
<212> TYPE: DNA
<213> ORGANISM: Heliothis virescens

<400> SEQUENCE: 22
actgacaagg atacaactag taaggac                                       27
```

```
<210> SEQ ID NO 23
<211> LENGTH: 27
<212> TYPE: DNA
<213> ORGANISM: Tenebrio molitor

<400> SEQUENCE: 23
ttcaaactga tcatctttag ttgggta                                      27

<210> SEQ ID NO 24
<211> LENGTH: 58
<212> TYPE: DNA
<213> ORGANISM: Tenebrio molitor

<400> SEQUENCE: 24
cgaattcgcc atggccactg acaaggatac aactagtaag gacaagttgc aatacaac    58

<210> SEQ ID NO 25
<211> LENGTH: 35
<212> TYPE: DNA
<213> ORGANISM: Tenebrio molitor

<400> SEQUENCE: 25
gcggcggcgc ggccgccttc aaactgatca tcttt                             35

<210> SEQ ID NO 26
<211> LENGTH: 39
<212> TYPE: DNA
<213> ORGANISM: Heliothis virescens

<400> SEQUENCE: 26
ggggtaccaa ctatgagatg gcagtcgacg tgagaatac                         39

<210> SEQ ID NO 27
<211> LENGTH: 29
<212> TYPE: DNA
<213> ORGANISM: Heliothis virescens

<400> SEQUENCE: 27
ggaattcatc ttgcgcgacc gttaaatga                                    29

<210> SEQ ID NO 28
<211> LENGTH: 915
<212> TYPE: DNA
<213> ORGANISM: Tenebrio molitor

<400> SEQUENCE: 28
actgacaagg atacaactag taaggacaag ttgcaataca acattgataa cattactcca    60
tctaacctcg acctggacat aaaatctgct tttaccatga atcgcaatc cggagatatt    120 acaattaatt ttgaagtcaa agacagcatg gagggttatt tcacgttaga tcttagtgtc    180
caggatgaag agccgaaaaa tcacaaagct gatgccactc taaaaattta tattgttact    240
agtaaaaaca ctgtagtgtt tagatttgaa aatgaccaag agaccgttag tgacaaagct    300
ggagatatta aaagtgtact ggatgaagaa tttcaatatg aaactaaagt cgaagctcca    360
acaggaaaca cgacagacgg tacacctctt acaaggtcac cggttttctt cctgaacttg    420
aacacaaatg aacctgtgga tgcaactgag atacttaaga agtcaccaa cgttgacgtg     480 ttccaaagat taaaaataa cttttcgaaa gttggtctgg tcttattgag ttttgattcc    540
agttccgaaa ccaacgaaaa cttggaagca attttgaaag cgtggttgat cggtgtttcg    600
gtagttctcg gagcactgtg tctcattctt ttgattgcgt ttatactgaa acgagagct    660 ttgaatcaac gtatcaagaa gctgtccagt accaaatttt cgggtcgcaa gagtcgggga    720
```

-continued

```
ttgaataggc aaggagtggc ggcccccaca accaacaaac acgccctaga aggatcaaat    780
ccagtgtcaa taacgaagtc gaccccgaag gacattgata ggacgagcgt cacgagcggc    840
gattcagatc taataggagt ggaagatgac gagaagtttg actttagtta cccaactaaa    900
gatgatcagt ttgaa                                                     915
```

CADHERIN RECEPTOR PEPTIDE FOR POTENTIATING BT BIOPESTICIDES

CROSS-REFERENCE TO RELATED APPLICATION

This present application claims priority under 35 U.S.C. §119(e) to U.S. Provisional Ser. No. 60/988,919, which was filed on Nov. 19, 2007, the disclosure of which is hereby incorporated by reference.

SEQUENCE LISTING SUBMISSION

The contents of the following SEQUENCE LISTING submission are incorporated herein by reference in its entirety: a computer readable form of the Sequence Listing submitted via EFS-Web on Mar. 6, 2009, containing the file name: "SequenceListing.txt" as a sequence listing, date recorded: Mar. 6, 2009, size: 29,124 bytes.

FIELD OF THE INVENTION

The present invention is directed to a novel cadherin fragment peptide derived from *Tenebrio molitor* larvae. Moreover, the peptide comprises a Cry3Aa toxin binding region from the full-length *T. molitor* cadherin and has synergistic characteristics of a binary toxin potentiating Cry3 and Cry1 toxins against coleopterans and lepidopteran species, respectively. Additionally, an identified functional receptor region in the protein can be used to screen insecticidal toxins for activity against various coleopterans and lepidoterans or increased potency.

BACKGROUND OF INVENTION

Leading biological based pesticide utilizes *Bacillus thuringiensis* (abbreviated herein as Bt) against lepidopterans, coleopterans, and other insect pests. The Gram-positive spore-forming bacterium produces parasporal protein crystals during stationary phase of the growth cycle. Genes encoding the crystals are categorized as cry genes. As a pesticide, the primary mode of action involves protein solubilization, proteolytic activation of the protoxin, binding to epithelial midgut receptor (cadherin), and subsequent pore formation and/or activation of intracellular cell-death signaling pathway. The use of Bt and its effectiveness as an insecticide is largely dependent on receptors in the target insect and the solubility of the Cry protein.

Coleopteran pests cause extensive damage to crops in the United States. For example, damage to corn crops occurs when rootworms feed on corn seedling roots. It has been estimated that rootworms cause in excess 1 billion dollars in damage to corn crops in the United States. (Meycalf, R. L., et al., 1986. Drysan, J. L. and T. A. Miller [Eds.], Springer-Verlag, New York, N.Y., pp. vii-xv.) Even with chemical insecticide applications of organophosphate or pyrethroid, rootworm damage still causes an estimated $750 million dollars annual damage to corn crops. One approach to combat rootworm damage while decreasing dependence of chemical pesticides is to express Bt protein in transgenic corn. For instance, Bt strain PS149B1 confers resistance to rootworms in corn plants (Moellenbeck, et al., 2001. *Nature Biotechnology*, 19:668-672). Additionally, U.S. Pat. Nos. 4,797,276 and 4,853,331 disclose a *Bacillus thuringiensis* strain *san diego*, (NRRL B-15939) that is effective in controlling corn rootworm, among other coleopteran species. Given the widespread damage caused by rootworm, there is continuing need to develop efficient biologically-based insecticides, specifically potentiating the usage of Bt toxin.

A lepidopteran pest is the pink bollworm (*Pectinophora gossypiella*). It is estimated that the preventive cost, damage control, and crop lost costs cotton growers over thirty-two million dollars annually (National Cotton Council, 2004). Cotton crop damage occurs when female bollworms lay their eggs in cotton bolls during the summer mating season. Resulting larvae feed on cotton seeds upon chewing and burrowing through cotton lint. Techniques to combat pink bollworm include releasing pheromones to disruption mating, releasing sterile males to disrupt mating patterns, chemical insecticide treatments, and planting of transgenic Bt cotton.

While Bt pesticides have been used against a narrow range of lepidopteran pests, the discovery that Bt can have a broader application towards other Orders of insects has prompted its use targeting other pests. (For instance, see U.S. Pat. Nos. 4,797,276 and 4,853,331). Also, it has been reported that the expression of Cry3Aa in transgenic potato cultivars are resistant to *Leptinotarsa decemlineata* while exerting a deleterious effect on the polyphagous moth *Spodoptera littoralis* (Hussein et al., 2006. *Journal of Chemical Ecology*, 32:1-13). Novel Bt isolates, new uses of known Bt isolates, and potentiating the toxicity of existing toxins remains an empirical, unpredictable art.

One approach to increase potency of Cry proteins against various insect pests is to utilize a Bt toxin receptor to potentiate toxicity to a target pest. The approach uses a peptide fragment derived from an insect cadherin protein combined with Cry protein toxin to increase a synergistic potency that would not be achieved via administration of the partial cadherin fragment or Cry protein individually.

BRIEF SUMMARY OF THE INVENTION

Disclosed is a novel cadherin peptide that enhances the toxicity of Cry proteins. An embodiment of the invention is a novel insecticide composition comprising an effective amount of cadherin peptide having SEQ. ID. NO:2 and an effective amount of *Bacillus thuringiensis* Cry protein. Furthermore, the effective amount of the composition would comprise a peptide with 90% amino acid sequence identity or greater with SEQ. ID. NO: 2. In one embodiment, the cadherin peptide and *Bacillus thuringiensis* Cry protein is administered at molar ratio range of approximately 1:2.5 to 1:200 respectively. In an embodiment, the Cry protein is a Cry3 protein or a Cry1 protein. In another embodiment, the composition is effective against coleopterans, namely *Tenebrio molitor*. It is also contemplated that the composition would be effective against other coleopteran pest such as *Agrilus planipennis, Agrilus marcopoli, Diabrotica* spp., and *Leptinotarsa decemlineata*. In another embodiment, the cadherin peptide increases the toxicity of *Bacillus thuringiensis* Cry proteins against lepidopterans, namely *Pectinophora gossypiella* and *Heliothis virescens*.

It is contemplated that the a composition comprising of cadherin peptide and Cry protein applied to the environment of the coleopteran pests, typically onto the foliage of the plant or crop to be protected by convention methods such as spraying. Other applications include, but are not limited to dusting, sprinkling, aerating, soil soaking, soil injection, seed coating, seedling coating, foliar spraying, misting, fumigating, aerosolizing may be required for application procedure well know to those skilled in the art.

The cadherin and Cry protein composition may be formulated for preventive or prophylactic application to an area to prevent infestation of pests.

In another embodiment, a method for inhibiting insect pests, the method comprising selecting a *Bacillus thuringiensis* Cry protein, potentiating said protein with an effective amount of cadherin peptide having SEQ. ID. NO: 2, and applying an effective amount of said Cry protein and cadherin peptide to the insect pest, wherein the mortality of said insect increases. It is contemplated that the cadherin peptide and *Bacillus thuringiensis* Cry protein is in a molar ratio range of approximately 1:2.5 to 1:200. For another embodiment, the cadherin peptide potentiates the insecticide activity of Cry proteins. The method is effective against insect pests of the order Coleoptera and Lepidoptera. It is contemplated that the cadherin peptide utilized in conjunction with other Cry proteins would be effective against other coleopteran pest such as *Agrilus planipennis, Agrilus marcopoli, Diabrotica* spp., and *Leptinotarsa decemlineata*. More particularly, the cadherin peptide is an isolated polypeptide (amino acid residues 1,322-1,516) comprising the Bt toxin binding site encoded by nucleotides 4,076-4,661 of SEQ ID NO: 3.

In another embodiment, a method for screening insecticidal toxins comprising transfecting cells to express base pairs 1322-1626 and 3969-4879 of SEQ. ID. NO: 3 or a fragment thereof sufficient to encode a functional protein, exposing said cells to a Cry toxin; and monitoring said cells for effect attributable to toxin exposure. In an embodiment for screening insecticidal toxins, the cell line is monitored via cytotoxicity assay. In another embodiment, the cells are transfected to express SEQ. ID. NO. 4 or a fragment thereof sufficient to encode a functional protein, exposing said cells to a Cry toxin; and monitoring said cells for effect attributable to toxin exposure. In another embodiment, the cells are transfected to express SEQ. ID. NO.: 28 or a fragment thereof sufficient to encode a functional protein, exposing said cells to a Cry toxin, and monitoring said cells for effect attributable to toxin exposure for screening insecticidal receptor.

BRIEF DESCRIPTION OF THE DRAWING

The present invention together with the above and other objects and advantages may best be understood from the following detailed description of the embodiment of the invention illustrated in the drawings, wherein:

FIG. 2 discloses the deduced amino acid sequence of the TmCad1p (SEQ ID NO: 1) as it exists expressed from pET151-D-TOPO expression vector. The TmCad1 peptide fragment corresponds to amino acid residues 1,322-1,516 of the full length protein (translation of nucleotides 4,076-4,661 of SEQ ID NO: 3). Bold letters and underline designates TmCad1 amino acids (195 residues), whereas 37 residues at amino terminus are from pET151-D-TOPO vector, including polyhistidine tag, V5 epitope tag, and TEV protease cleavage site.

FIG. 5A depicts molar ratios of 1:20 Cry3Aa:rTmCad1p, with FIG. 5B depicting molar ratios 1:20 and 1:200 Cry3Aa:rTmCad1p, and FIG. 5C depicting molar ratios of 1:20 Cry3Aa:rTmCad1p. rTmCad1p utilized in FIG. 5 were obtained from *E. coli*. ArcticExpress (DE3).

Figure 9:
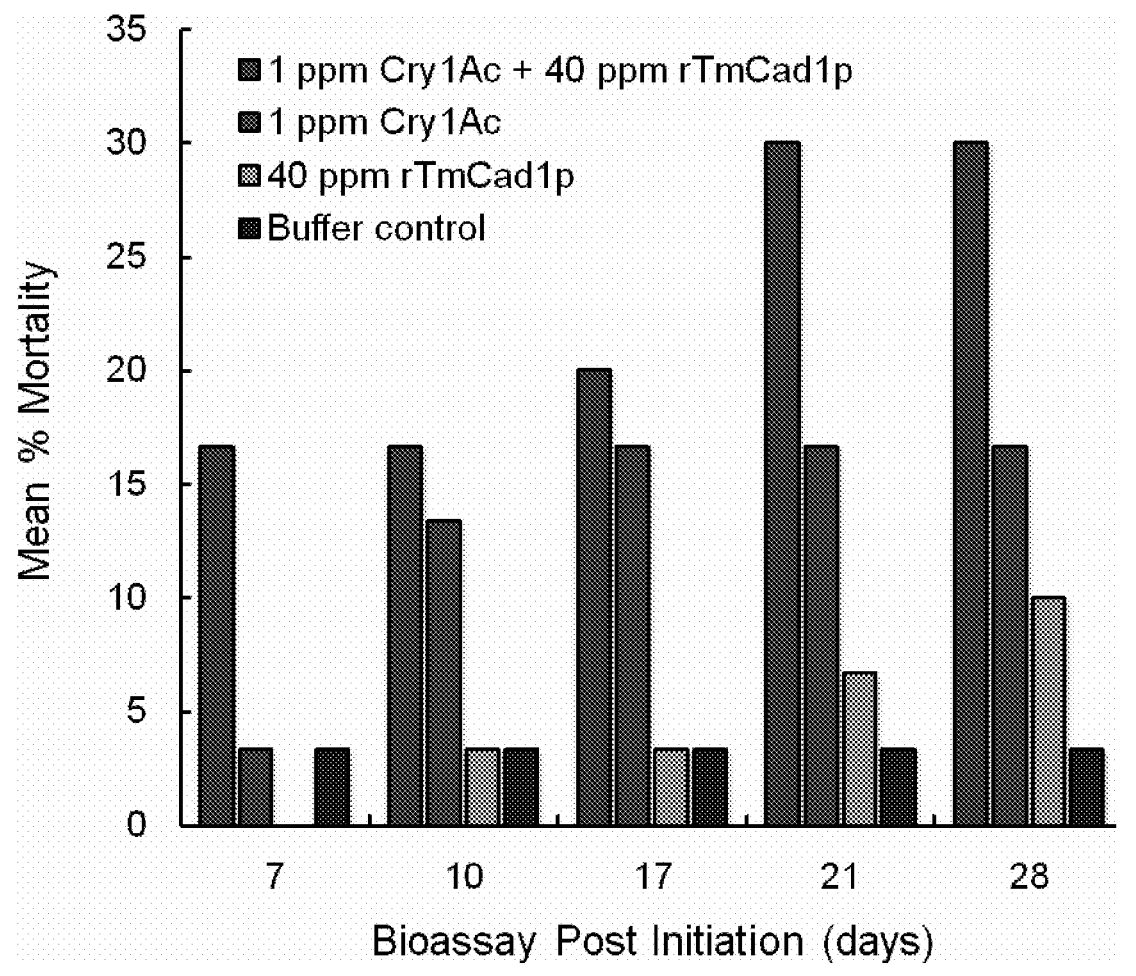

FIG. 9 is a graph of percentages of *Pectinophora gossypiella* (PBW) larval mortality on a Cry1 Ac-resistant strain (AZP-R). Results of single bioassay replicate ($n=30$ insects per treatment) on Cry1Ac-resistant PBW larvae (from AZP-R strain) with 200-fold (molar ratio) rTmCad1p (expressed from *E. coli* Arctic-Express (DE3)) and Cry1Ac crystalline protoxin (HD-73 preparation).

BRIEF DESCRIPTION OF THE SEQUENCES

Figure 1A:
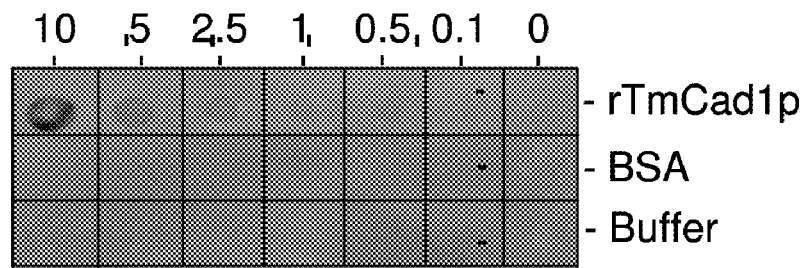
FIG. 1A is a digital image of dot blot assay of 0.1, 0.5, 1, 2.5, 5, and 10 μg of rTmCad1 peptide fragment (rTmCad1p) spotted onto PVDF membrane, blocked with bovine serum albumin, and incubated with Cry3Aa. Binding of rTmCad1p fragment to Cry3Aa toxin was detected by incubations in rabbit anti-Cry3Aa and ECL horseradish peroxidase (HRP)-labeled anti-rabbit antisera (Amersham), followed by detection of HRP activity in ECL substrate solution (Amersham RPN2209).

SEQ. ID. NO: 1: is the nucleotide sequence that encodes for a cadherin fragment obtained from *Tenebrio molitor* larvae.

SEQ. ID. NO: 2: is the deduced amino acid sequence of a cadherin fragment obtained from *Tenebrio molitor* larvae (rTmCad1p).

SEQ. ID. NO: 3: is the complementary nucleotide sequence that encodes for a cadherin obtained from *Tenebrio molitor* larvae.

SEQ. ID. NO: 4: is the deduced amino acid sequence for a complete cadherin obtained from *Tenebrio molitor* larvae.

SEQ. ID. NO: 5: is the nucleotide sequence for PCR primer Tm1.

SEQ. ID. NO: 6: is the nucleotide sequence for PCR primer Tm2.

SEQ. ID. NO: 7: is the nucleotide sequence for PCR primer Tm3.

SEQ. ID. NO: 8: is the nucleotide sequence for PCR primer Tm4.

SEQ. ID. NO: 9: is the nucleotide sequence for PCR primer Tm5.

SEQ. ID. NO: 10: is the nucleotide sequence for PCR primer Tm6.

SEQ. ID. NO: 11: is the nucleotide sequence for PCR primer Tm7.

SEQ. ID. NO: 12: is the nucleotide sequence for PCR primer Tm8.

SEQ. ID. NO: 13: is the nucleotide sequence for PCR primer Tm9.

SEQ. ID. NO: 14: is the nucleotide sequence for PCR primer Tm10.

SEQ. ID. NO: 15: is the nucleotide sequence for PCR primer Tm11.

SEQ. ID. NO: 16: is the nucleotide sequence for PCR primer Tm12.

SEQ. ID. NO: 17: is the nucleotide sequence for PCR primer Tm13.

SEQ. ID. NO: 18: is the nucleotide sequence for PCR primer Tm14.

SEQ. ID. NO: 19: is the nucleotide sequence for PCR primer Tm15.

SEQ. ID. NO: 20: is the nucleotide sequence for PCR primer Tm16.

SEQ. ID. NO: 21: is the nucleotide sequence for PCR primer Tm17.

SEQ. ID. NO: 22: is the nucleotide sequence for PCR primer Tm18

SEQ. ID. NO: 23: is the nucleotide sequence for PCR primer Tm19

SEQ. ID. NO: 24: is the nucleotide sequence for PCR primer Tm20.

SEQ. ID. NO: 25: is the nucleotide sequence for PCR primer Tm21.

SEQ. ID. NO: 26: is the nucleotide sequence for PCR primer Hv1.

SEQ. ID. NO: 27: is the nucleotide sequence for PCR primer Hv2.

SEQ. ID. NO 28: is the nucleotide sequence listing for TmCad1EC12-cyto.

DETAILED DESCRIPTION OF THE INVENTION

Definitions

As used in the specification and claims, the singular form "a", "an" and "the" include plural references unless the context clearly dictates otherwise. For example, the term "a cell" includes a plurality of cells, including mixtures thereof.

"*Bacillus thuringiensis*" or "Bt" refers to Gram-positive bacterium that upon sporulation form proteinaceous delta-endotoxins that are insecticidal towards lepidopterans, dipterans, and coleopterans, depending on the delta-endotoxin.

A "composition" is intended to mean a combination of active agent and another compound or composition, inert (for example, a detectable agent or label) or active, such as an adjuvant. A compound can comprise multiple moieties, including a mixture of Cry toxin and a potentiating peptide.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction (PCR), or a combination thereof. The present invention embodies utilizing the oligonucleotide as a primer for DNA synthesis for cloning purposes or as template for protein synthesis using *Escherichia coli* heterologous expression system. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

An "effective amount" is an amount sufficient to effect beneficial or desired results. An effective amount can be administered in one or more administrations. In terms of administering an "effective amount", such an amount sufficient to reverse, slow, or delay the growth of a coleopteran or lepidopteran pests in an adult stage or a larvae stage would be an effective amount. Table I lists of currently known delta-endotoxins with GenBank accession numbers for sequenced polypeptides and polynucleotides. In a preferred embodiment, the invention discloses a novel peptide, rTmCad1p, is mixed with Cry3Aa to potentiate the Cry3Aa toxin. In another embodiment, rTmCad1p is mixed with Cry1Ac protoxin to potentiate larval mortality.

TABLE 1

List of known *B. thuringiensis* endotoxins

| NAME | GenBank Accession Number |
|---|---|
| Cry1Aa1 | M11250 |
| Cry1Aa2 | M10917 |
| Cry1Aa3 | D00348 |
| Cry1Aa4 | X13535 |
| Cry1Aa5 | D17518 |
| Cry1Aa6 | U43605 |
| Cry1Aa7 | AF081790 |
| Cry1Aa8 | I26149 |
| Cry1Aa9 | AB026261 |
| Cry1Aa10 | AF154676 |
| Cry1Aa11 | Y09663 |
| Cry1Aa12 | AF384211 |
| Cry1Aa13 | AF510713 |
| Cry1Aa14 | AY197341 |
| Cry1Aa15 | DQ062690 |
| Cry1Ab1 | M13898 |
| Cry1Ab2 | M12661 |
| Cry1Ab3 | M15271 |
| Cry1Ab4 | D00117 |
| Cry1Ab5 | X04698 |
| Cry1Ab6 | M37263 |
| Cry1Ab7 | X13233 |
| Cry1Ab8 | M16463 |
| Cry1Ab9 | X54939 |
| Cry1Ab10 | A29125 |
| Cry1Ab11 | I12419 |

TABLE 1-continued

List of known *B. thuringiensis* endotoxins

| NAME | GenBank Accession Number |
|---|---|
| Cry1Ab12 | AF059670 |
| Cry1Ab13 | AF254640 |
| Cry1Ab14 | U94191 |
| Cry1Ab15 | AF358861 |
| Cry1Ab16 | AF375608 |
| Cry1Ab17 | AAT46415 |
| Cry1Ab18 | AAQ88259 |
| Cry1Ab19 | AY847289 |
| Cry1Ab20 | DQ241675 |
| Cry1Ab21 | EF683163 |
| Cry1Ab22 | ABW87320 |
| Cry1Ab-like | AF327924 |
| Cry1Ab-like | AF327925 |
| Cry1Ab-like | AF327926 |
| Cry1Ab-like | DQ781309 |
| Cry1Ac1 | M11068 |
| Cry1Ac2 | M35524 |
| Cry1Ac3 | X54159 |
| Cry1Ac4 | M73249 |
| Cry1Ac5 | M73248 |
| Cry1Ac6 | U43606 |
| Cry1Ac7 | U87793 |
| Cry1Ac8 | U87397 |
| Cry1Ac9 | U89872 |
| Cry1Ac10 | AJ002514 |
| Cry1Ac11 | AJ130970 |
| Cry1Ac12 | I12418 |
| Cry1Ac13 | AF148644 |
| Cry1Ac14 | AF492767 |
| Cry1Ac15 | AY122057 |
| Cry1Ac16 | AY730621 |
| Cry1Ac17 | AY925090 |
| Cry1Ac18 | DQ023296 |
| Cry1Ac19 | DQ195217 |
| Cry1Ac20 | DQ285666 |
| Cry1Ac21 | DQ062689 |
| Cry1Ac22 | EU282379 |
| Cry1Ac23 | AM949588 |
| Cry1Ac24 | ABL01535 |
| Cry1Ad1 | M73250 |
| Cry1Ad2 | A27531 |
| Cry1Ae1 | M65252 |
| Cry1Af1 | U82003 |
| Cry1Ag1 | AF081248 |
| Cry1Ah1 | AF281866 |
| Cry1Ah2 | DQ269474 |
| Cry1Ai1 | AY174873 |
| Cry1A-like | AF327927 |
| Cry1Ba1 | X06711 |
| Cry1Ba2 | X95704 |
| Cry1Ba3 | AF368257 |
| Cry1Ba4 | AF363025 |
| Cry1Ba5 | ABO20894 |
| Cry1Ba6 | ABL60921 |
| Cry1Bb1 | L32020 |
| Cry1Bc1 | Z46442 |
| Cry1Bd1 | U70726 |
| Cry1Bd2 | AY138457 |
| Cry1Be1 | AF077326 |
| Cry1Be2 | AAQ52387 |
| Cry1Bf1 | AX189649 |
| Cry1Bf2 | AAQ52380 |
| Cry1Bg1 | AY176063 |
| Cry1Ca1 | X07518 |
| Cry1Ca2 | X13620 |
| Cry1Ca3 | M73251 |
| Cry1Ca4 | A27642 |
| Cry1Ca5 | X96682 |
| Cry1Ca6 [1] | AF215647 |
| Cry1Ca7 | AY015492 |
| Cry1Ca8 | AF362020 |
| Cry1Ca9 | AY078160 |
| Cry1Ca10 | AF540014 |
| Cry1Ca11 | AY955268 |
| Cry1Cb1 | M97880 |
| Cry1Cb2 | AY007686 |
| Cry1Cb3 | EU679502 |
| Cry1Cb-like | AAX63901 |
| Cry1Da1 | X54160 |
| Cry1Da2 | I76415 |
| Cry1Db1 | Z22511 |
| Cry1Db2 | AF358862 |
| Cry1Dc1 | EF059913 |
| Cry1Ea1 | X53985 |
| Cry1Ea2 | X56144 |
| Cry1Ea3 | M73252 |
| Cry1Ea4 | U94323 |
| Cry1Ea5 | A15535 |
| Cry1Ea6 | AF202531 |
| Cry1Ea7 | AAW72936 |
| Cry1Ea8 | ABX11258 |
| Cry1Eb1 | M73253 |
| Cry1Fa1 | M63897 |
| Cry1Fa2 | M73254 |
| Cry1Fb1 | Z22512 |
| Cry1Fb2 | AB012288 |
| Cry1Fb3 | AF062350 |
| Cry1Fb4 | I73895 |
| Cry1Fb5 | AF336114 |
| Cry1Fb6 | EU679500 |
| Cry1Fb7 | EU679501 |
| Cry1Ga1 | Z22510 |
| Cry1Ga2 | Y09326 |
| Cry1Gb1 | U70725 |
| Cry1Gb2 | AF288683 |
| Cry1Gc | AAQ52381 |
| Cry1Ha1 | Z22513 |
| Cry1Hb1 | U35780 |
| Cry1H-like | AF182196 |
| Cry1Ia1 | X62821 |
| Cry1Ia2 | M98544 |
| Cry1Ia3 | L36338 |
| Cry1Ia4 | L49391 |
| Cry1Ia5 | Y08920 |
| Cry1Ia6 | AF076953 |
| Cry1Ia7 | AF278797 |
| Cry1Ia8 | AF373207 |
| Cry1Ia9 | AF521013 |
| Cry1Ia10 | AY262167 |
| Cry1Ia11 | AJ315121 |
| Cry1Ia12 | AAV53390 |
| Cry1Ia13 | ABF83202 |
| Cry1Ia14 | EU887515 |
| Cry1Ib1 | U07642 |
| Cry1Ib2 | ABW88019 |
| Cry1Ib3 | EU677422 |
| Cry1Ic1 | AF056933 |
| Cry1Ic2 | AAE71691 |
| Cry1Id1 | AF047579 |
| Cry1Ie1 | AF211190 |
| Cry1If1 | AAQ52382 |
| Cry1I-like | I90732 |
| Cry1I-like | DQ781310 |
| Cry1Ja1 | L32019 |
| Cry1Jb1 | U31527 |
| Cry1Jc1 | I90730 |
| Cry1Jc2 | AAQ52372 |
| Cry1Jd1 | AX189651 |
| Cry1Ka1 | U28801 |
| Cry1La1 | AAS60191 |
| Cry1-like | I90729 |
| Cry2Aa1 | M31738 |
| Cry2Aa2 | M23723 |
| Cry2Aa3 | D86064 |
| Cry2Aa4 | AF047038 |
| Cry2Aa5 | AJ132464 |
| Cry2Aa6 | AJ132465 |
| Cry2Aa7 | AJ132463 |
| Cry2Aa8 | AF252262 |
| Cry2Aa9 | AF273218 |
| Cry2Aa10 | AF433645 |
| Cry2Aa11 | AAQ52384 |

TABLE 1-continued

List of known *B. thuringiensis* endotoxins

| NAME | GenBank Accession Number |
|---|---|
| Cry2Aa12 | DQ977646 |
| Cry2Aa13 | ABL01536 |
| Cry2Aa14 | ACF04939 |
| Cry2Ab1 | M23724 |
| Cry2Ab2 | X55416 |
| Cry2Ab3 | AF164666 |
| Cry2Ab4 | AF336115 |
| Cry2Ab5 | AF441855 |
| Cry2Ab6 | AY297091 |
| Cry2Ab7 | DQ119823 |
| Cry2Ab8 | DQ361266 |
| Cry2Ab9 | DQ341378 |
| Cry2Ab10 | EF157306 |
| Cry2Ab11 | AM691748 |
| Cry2Ab12 | ABM21764 |
| Cry2Ab13 | EU909454 |
| Cry2Ab14 | EU909455 |
| Cry2Ac1 | X57252 |
| Cry2Ac2 | AY007687 |
| Cry2Ac3 | AAQ52385 |
| Cry2Ac4 | DQ361267 |
| Cry2Ac5 | DQ341379 |
| Cry2Ac6 | DQ359137 |
| Cry2Ac7 | AM292031 |
| Cry2Ac8 | AM421903 |
| Cry2Ac9 | AM421904 |
| Cry2Ac10 | BI 877475 |
| Cry2Ac11 | AM689531 |
| Cry2Ac12 | AM689532 |
| Cry2Ad1 | AF200816 |
| Cry2Ad2 | DQ358053 |
| Cry2Ad3 | AM268418 |
| Cry2Ad4 | AM490199 |
| Cry2Ad5 | AM765844 |
| Cry2Ae1 | AAQ52362 |
| Cry2Af1 | EF439818 |
| Cry2Ag | ACH91610 |
| Cry2Ah | EU939453 |
| Cry3Aa1 | M22472 |
| Cry3Aa2 | J02978 |
| Cry3Aa3 | Y00420 |
| Cry3Aa4 | M30503 |
| Cry3Aa5 | M37207 |
| Cry3Aa6 | U10985 |
| Cry3Aa7 | AJ237900 |
| Cry3Aa8 | AAS79487 |
| Cry3Aa9 | AAW05659 |
| Cry3Aa10 | AAU29411 |
| Cry3Aa11 | AY882576 |
| Cry3Aa12 | ABY49136 |
| Cry3Ba1 | X17123 |
| Cry3Ba2 | A07234 |
| Cry3Bb1 | M89794 |
| Cry3Bb2 | U31633 |
| Cry3Bb3 | I15475 |
| Cry3Ca1 | X59797 |
| Cry4Aa1 | Y00423 |
| Cry4Aa2 | D00248 |
| Cry4Aa3 | AL731825 |
| Cry4A-like | DQ078744 |
| Cry4Ba1 | X07423 |
| Cry4Ba2 | X07082 |
| Cry4Ba3 | M20242 |
| Cry4Ba4 | D00247 |
| Cry4Ba5 | AL731825 |
| Cry4Ba-like | ABC47686 |
| Cry4Ca1 | EU646202 |
| Cry5Aa1 | L07025 |
| Cry5Ab1 | L07026 |
| Cry5Ac1 | I34543 |
| Cry5Ad1 | EF219060 |
| Cry5Ba1 | U19725 |
| Cry5Ba2 | EU121522 |
| Cry6Aa1 | L07022 |
| Cry6Aa2 | AF499736 |
| Cry6Aa3 | DQ835612 |

TABLE 1-continued

List of known *B. thuringiensis* endotoxins

| NAME | GenBank Accession Number |
|---|---|
| Cry6Ba1 | L07024 |
| Cry7Aa1 | M64478 |
| Cry7Ab1 | U04367 |
| Cry7Ab2 | U04368 |
| Cry7Ab3 | BI 1015188 |
| Cry7Ab4 | EU380678 |
| Cry7Ab5 | ABX79555 |
| Cry7Ab6 | FJ194973 |
| Cry7Ba1 | ABB70817 |
| Cry7Ca1 | EF486523 |
| Cry8Aa1 | U04364 |
| Cry8Ab1 | EU044830 |
| Cry8Ba1 | U04365 |
| Cry8Bb1 | AX543924 |
| Cry8Bc1 | AX543926 |
| Cry8Ca1 | U04366 |
| Cry8Ca2 | AAR98783 |
| Cry8Ca3 | EU625349 |
| Cry8Da1 | AB089299 |
| Cry8Da2 | BD133574 |
| Cry8Da3 | BD133575 |
| Cry8Db1 | AB303980 |
| Cry8Ea1 | AY329081 |
| Cry8Ea2 | EU047597 |
| Cry8Fa1 | AY551093 |
| Cry8Ga1 | AY590188 |
| Cry8Ga2 | DQ318860 |
| Cry8Ga3 | FJ198072 |
| Cry8Ha1 | EF465532 |
| Cry8Ia1 | EU381044 |
| Cry8Ja1 | EU625348 |
| Cry8 like | ABS53003 |
| Cry9Aa1 | X58120 |
| Cry9Aa2 | X58534 |
| Cry9Aa like | AAQ52376 |
| Cry9Ba1 | X75019 |
| Cry9Bb1 | AY758316 |
| Cry9Ca1 | Z37527 |
| Cry9Ca2 | AAQ52375 |
| Cry9Da1 | D85560 |
| Cry9Da2 | AF042733 |
| Cry9Db1 | AY971349 |
| Cry9Ea1 | AB011496 |
| Cry9Ea2 | AF358863 |
| Cry9Ea3 | EF157307 |
| Cry9Ea4 | EU760456 |
| Cry9Ea5 | EU789519 |
| Cry9Ea6 | EU887516 |
| Cry9Eb1 | AX189653 |
| Cry9Ec1 | AF093107 |
| Cry9Ed1 | AY973867 |
| Cry9 like | AF093107 |
| Cry10Aa1 | M12662 |
| Cry10Aa2 | E00614 |
| Cry10Aa3 | AL731825 |
| Cry10A like | DQ167578 |
| Cry11Aa1 | M31737 |
| Cry11Aa2 | M22860 |
| Cry11Aa3 | AL731825 |
| Cry11Aa-like | DQ166531 |
| Cry11Ba1 | X86902 |
| Cry11Bb1 | AF017416 |
| Cry12Aa1 | L07027 |
| Cry13Aa1 | L07023 |
| Cry14Aa1 | U13955 |
| Cry15Aa1 | M76442 |
| Cry16Aa1 | X94146 |
| Cry17Aa1 | X99478 |
| Cry18Aa1 | X99049 |
| Cry18Ba1 | AF169250 |
| Cry18Ca1 | AF169251 |
| Cry19Aa1 | Y07603 |
| Cry19Ba1 | D88381 |
| Cry20Aa1 | U82518 |
| Cry21Aa1 | I32932 |
| Cry21Aa2 | I66477 |

TABLE 1-continued

List of known *B. thuringiensis* endotoxins

| NAME | GenBank Accession Number |
|---|---|
| Cry21Ba1 | AB088406 |
| Cry22Aa1 | I34547 |
| Cry22Aa2 | AX472772 |
| Cry22Aa3 | EU715020 |
| Cry22Ab1 | AAK50456 |
| Cry22Ab2 | AX472764 |
| Cry22Ba1 | AX472770 |
| Cry23Aa1 | AAF76375 |
| Cry24Aa1 | U88188 |
| Cry24Ba1 | BAD32657 |
| Cry24Ca1 | AM158318 |
| Cry25Aa1 | U88189 |
| Cry26Aa1 | AF122897 |
| Cry27Aa1 | AB023293 |
| Cry28Aa1 | AF132928 |
| Cry28Aa2 | AF285775 |
| Cry29Aa1 | AJ251977 |
| Cry30Aa1 | AJ251978 |
| Cry30Ba1 | BAD00052 |
| Cry30Ca1 | BAD67157 |
| Cry30Da1 | EF095955 |
| Cry30Db1 | BAE80088 |
| Cry30Ea1 | EU503140 |
| Cry30Fa1 | EU751609 |
| Cry30Ga1 | EU882064 |
| Cry31Aa1 | AB031065 |
| Cry31Aa2 | AY081052 |
| Cry31Aa3 | AB250922 |
| Cry31Aa4 | AB274826 |
| Cry31Aa5 | AB274827 |
| Cry31Ab1 | AB250923 |
| Cry31Ab2 | AB274825 |
| Cry31Ac1 | AB276125 |
| Cry32Aa1 | AY008143 |
| Cry32Ba1 | BAB78601 |
| Cry32Ca1 | BAB78602 |
| Cry32Da1 | BAB78603 |
| Cry33Aa1 | AAL26871 |
| Cry34Aa1 | AAG50341 |
| Cry34Aa2 | AAK64560 |
| Cry34Aa3 | AY536899 |
| Cry34Aa4 | AY536897 |
| Cry34Ab1 | AAG41671 |
| Cry34Ac1 | AAG50118 |
| Cry34Ac2 | AAK64562 |
| Cry34Ac3 | AY536896 |
| Cry34Ba1 | AAK64565 |
| Cry34Ba2 | AY536900 |
| Cry34Ba3 | AY536898 |
| Cry35Aa1 | AAG50342 |
| Cry35Aa2 | AAK64561 |
| Cry35Aa3 | AY536895 |
| Cry35Aa4 | AY536892 |
| Cry35Ab1 | AAG41672 |
| Cry35Ab2 | AAK64563 |
| Cry35Ab3 | AY536891 |
| Cry35Ac1 | AAG50117 |
| Cry35Ba1 | AAK64566 |
| Cry35Ba2 | AY536894 |
| Cry35Ba3 | AY536893 |
| Cry36Aa1 | AAK64558 |
| Cry37Aa1 | AAF76376 |
| Cry38Aa1 | AAK64559 |
| Cry39Aa1 | BAB72016 |
| Cry40Aa1 | BAB72018 |
| Cry40Ba1 | BAC77648 |
| Cry40Ca1 | EU381045 |
| Cry40Da1 | EU596478 |
| Cry41Aa1 | AB116649 |
| Cry41Ab1 | AB116651 |
| Cry42Aa1 | AB116652 |
| Cry43Aa1 | AB115422 |
| Cry43Aa2 | AB176668 |
| Cry43Ba1 | AB115422 |
| Cry43-like | AB115422 |
| Cry44Aa | BAD08532 |
| Cry45Aa | BAD22577 |
| Cry46Aa | BAC79010 |
| Cry46Aa2 | BAG68906 |
| Cry46Ab | BAD35170 |
| Cry47Aa | AY950229 |
| Cry48Aa | AJ841948 |
| Cry48Aa2 | AM237205 |
| Cry48Aa3 | AM237206 |
| Cry48Ab | AM237207 |
| Cry48Ab2 | AM237208 |
| Cry49Aa | AJ841948 |
| Cry49Aa2 | AM237201 |
| Cry49Aa3 | AM237203 |
| Cry49Aa4 | AM237204 |
| Cry49Ab1 | AM237202 |
| Cry50Aa1 | AB253419 |
| Cry51Aa1 | DQ836184 |
| Cry52Aa1 | EF613489 |
| Cry53Aa1 | EF633476 |
| Cry54Aa1 | EU339367 |
| Cry55Aa1 | EU121521 |
| Cry55Aa2 | AAE33526 |

It should similarly be noted that one skilled in the art, having the benefit of the subject disclosure, will recognize that the subject peptides potentially have a variety of functions, uses, and activities. As stated herein, the subject peptides can be administered together with a Cry protein. When used in this manner, peptides of the subject invention can effect a faster kill of the targeted insects, and/or they can enable less Cry protein to be required for killing the insects. Complete lethality, however, is not required. The ultimate preferred goal is to prevent insects from damaging plants of interest. Thus, prevention of feeding is sufficient. Thus "inhibiting" the insects is all that is required. This can be accomplished by making the insects "sick" or by otherwise inhibiting (including killing) them so that damage to the plants being protected is reduced. This includes inhibiting larval growth of target pests or causing larval mortality. Thus, the inhibitory function of the subject peptides can be achieved by any mechanism of action, directly or indirectly related to the Cry protein, or completely independent of the Cry protein.

It is contemplated TmCad1 would potentiate toxicity of Cry delta-endotoxins such as but not limited to Cry1A, Cry1B, Cry1I, Cry1J, Cry2A, Cry3A, Cry3A, Cry3B, Cry3C, Cry7A, Cry8A, Cry8B, Cry8C, Cry8D, Cry15A, Cry18A, Cry34A, Cry34B, Cry35A, Cry 35B. Additionally, polynucleotide of Bt toxins yet to be discovered or active fragments thereof would potentiate toxicity with the novel peptide. Accordingly, the skilled artisan would potentiate Bt toxins with the teachings disclosed herein.

Those trained in the art will recognize that nucleotide sequences including that encoding for TmCad1 will encode for amino acids with equivalent biological activity. Allelic variation may occur in the DNA sequences but will likely not change toxin-binding or potentiation activity of rTmCad1. DNA sequences having at least 90% identity to the included sequences are considered equivalent sequences and are included in the subject invention.

Chymotrypsin was from Worthington (Lakewood, N.J.). All other chemicals were from Sigma Chemical Co. (St. Louis, Mo.).

This invention is directed to a novel polypeptide that potentiates Bt toxin. The cDNA that encodes this polypeptide was derived from a *Tenebrio molitor* larval midgut library, which is of the Order Coleoptera. Gene-specific primers were designed and the complete coding sequence (tmcad1) was obtained from larval midgut cDNA by 5'- and 3'-RACE using the GeneRacer kit from Invitrogen (Carlsbad, Calif.) and SuperTaq Plus DNA polymerase (Ambion, Austin, Tex.). Tm1 and Tm2 nucleotide primers (Table 2) were designed from a partial tmcad1 cDNA, originally obtained from randomly selected clones from a *T. molitor* larval midgut library. Tm1 and Tm2 are in the sense orientation and were used with the GeneRacer 3'-primer to amplify the 3' end. Similarly, PCR primers were designed in the antisense orientation (Tm3, Tm4, Tm5, Tm6, Tm7, Tm8, Tm9, Tm10; Table 2) and were used with the GeneRacer 5'-primer and GeneRacer 5'-nested primer to amplify the missing 5' cDNA fragments. PCR products were gel-purified and inserted into pCR2.1-TOPO or pCR4-TOPO cloning vectors. Oligonucleotide primers (Tm11, Tm12, Tm13, Tm14, Tm15) were designed from known tmcad1 and used to sequence missing internal regions of subcloned cDNA. A cDNA containing the entire *T. molitor* cadherin (tmcad1) coding sequence was obtained by RT-PCR and confirmed that our results from RACE are consistent with a single, continuous cadherin cDNA. DNA sequencing was performed using the GenomeLab DTCS Quick Start Kit on a CEQ8000 DNA sequencer (Beckman-Coulter, Fullerton, Calif.). The complete tmcad1 cDNA sequence was deposited in the NCBI database (accession DQ988044).

TABLE 2

| Primer | Orientation | Position | Primer DNA Sequence |
|---|---|---|---|
| Tm1-SEQ. ID. NO: 5 | Sense | 4538-4563 | 5'-TGAAAGCGTGGTTGATCGGTGTTTCG-3' |
| Tm2-SEQ. ID. NO: 6 | Sense | 4648-4676 | 5'-TCCAGTACCAAATTCGGGTCGCAAGAG-3' |
| Tm3-SEQ. ID. NO: 7 | Antisense | 4152-4179 | 5'-GGCATCAGCTTTGTGATTTTCCGGCTCT-3' |
| Tm4-SEQ. ID. NO: 8 | Antisense | 4018-4042 | 5'-TGTCCAGGTCGAGGTTAGATGGAGT-3' |
| Tm5-SEQ. ID. NO: 9 | Antisense | 4055-4079 | 5'-TCTCCGGATTGCGTATTCATGGTAA-3' |
| Tm6-SEQ. ID. NO: 10 | Antisense | 3864-3893 | 5'-TCAAACACTGGAGATTCGTCGTTCTGGTCT-3' |
| Tm7-SEQ. ID. NO: 11 | Antisense | 3788-3811 | 5'-GCTTGTCAGCGTTAGATGACTGAA-3' |
| Tm8-SEQ. ID. NO: 12 | Antisense | 3734-3753 | 5'-GAGCGGTTGTTTAAGGGTGA-3' |
| Tm9-SEQ. ID. NO: 13 | Antisense | 2905-2928 | 5'-TGTCACCTTCATCGTCATCTTTCC-3' |
| Tm10-SEQ. ID. NO: 14 | Antisense | 1388-1412 | 5'-TCATCGTTGCATATCATTTAGGTTGA-3' |
| Tm11-SEQ. ID. NO: 15 | Sense | 1830-1853 | 5'-CGACGCAGATTTGGAGTTCTCGAT-3' |
| Tm12-SEQ. ID. NO: 16 | Antisense | 2267-2290 | 5'-CAACCCAGTCGGGAGTGTTCTCAT-3' |
| Tm13-SEQ. ID. NO: 17 | Sense | 377-404 | 5'-TCAAGAACTTGGACGACGAACATCCGAC-3' |
| Tm14-SEQ. ID. NO: 18 | Antisense | 883-909 | 5'-GGCATCCACCGTAGCGAAGTTGTTCTC-3' |
| Tm15-SEQ. ID. NO: 19 | Antisense | 1023-1044 | 5'-AATGTCTTCAAGGATCAGCAGT-3' |
| Tm16-SEQ. ID. NO: 20 | Sense | Adapter | 5'-CACCGAGCACGAGGACACTGACAT-3' |
| Tm17-SEQ. ID. NO: 21 | Antisense | 4526-4548 | 5'-CTACCACGCTTTCAAAATTGCTTCCA-3' |
| Tm18-SEQ. ID. NO: 22 | Sense | 3964-3990 | 5'-ACTGACAAGGATACAACTAGTAAGGAC-3' |
| Tm19-SEQ. ID. NO: 23 | Antisense | 4852-4878 | 5'-TTCAAACTGATCATCTTTAGTTGGGTA-3' |
| Tm20-SEQ. ID. NO: 24 | Sense | 3961-4005 | 5'-CGAATTCGCCATGGCCACTGACAAGGATACA ACTAGTAAGGACAAGTTGCAATACAAC-3' |

TABLE 2-continued

| Primer | Orientation | Position | Primer DNA Sequence |
|---|---|---|---|
| Tm21-SEQ. ID. NO: 25 | Antisense | 4861-4878 | 5'-GCGGCGGCGCGGCCGCCTTCAAACTGATCAT CTTT-3' |
| Hv1-SEQ. ID. NO: 26 | Sense | 1-31 | 5'-GGGGTACCAACTATGAGATGGCAGTCGACGT GAGAATAC-3' |
| Hv2-SEQ. ID. NO: 27 | Antisense | 59-81 | 5'-GGAATTCATCTTGCGCGACCGTTAAATGA-3' |

The full-length cDNA, tmcad1, is 5,095 bp and contains an open reading frame of 4,881 bp that encode for 1,626 amino acid residues. TmCad1 has a predicted pI of 4.13 and expected molecular mass of 179,341 kDa. TmCad1 was predicted to have extracellular, transmembrane, and intracellular domains using TMHMM Server v 2. (http://www.cbs.dtu.dk/services/TMHMM-2.0/; an available web-based server for the prediction of transmembrane helices in proteins) and 12 cadherin repeat domains using Motif Scan of PROSITE database (http://myhits.isb-sib.ch/cgi-bin/motif_scan; an available web-based server for scanning sequences for all known protein motifs).

PCR and KOD high-fidelity DNA polymerase (EMD Biosciences, San Diego, Calif.) was used to amplify 585 bp product from cDNA encoding for the partial TmCad1 (nucleotides 4,076-4,661 from SEQ. ID. NO: 3 that correspond to amino acid residues 1,322-1,516). PCR product generated using the primers Tm16 and Tm17 was gel-purified and inserted into the *Escherichia coli* expression vector pET151-D-TOPO (Invitrogen). Insertion of the correct sequence into the expression vector was confirmed by sequencing DNA in both directions with T7 and T7rev vector primers.

Peptide Expression Via *E. Coli* BL21 Transformation

For expression of the rTmCad1 peptide fragment, BL21 Star (DE3) *E. coli* was transformed and cultures were grown as previously outlined (Fabrick and Tabashnik, 2007, *Insect Biochem. Mol. Biol.* 37(2):97-106). Because the pET151-D-TOPO vector produces recombinant protein containing an amino-terminal six-histidine tag (see FIG. 2), $Ni^{2+}$-affinity chromatography was used to purify 6His-rTmCad1 peptide (6His-rTmCad1p). Protein was extracted from *E. coli* inclusion bodies and purification was performed under hybrid denaturing/native conditions as previously described in Fabrick and Tabashnik, 2007, *Insect Biochem. Mol. Biol.* 37(2): 97-106 and incorporated herein by reference. Elution fractions containing 6His-rTmCad1p were pooled and dialyzed against 0.01 M Tris-HCl, pH 8.0, 0.01% Triton X100.

rAcTEV protease (Invitrogen) can be used to remove 27 amino acid residues at the amino terminus of 6His-rTmCad1p, which included the six histidine tag and a V5 epitope (See FIG. 2). Bioassays as detailed infra, utilized unhydrolyzed rTmCAD1p.

Purification of rAcTEV protease-treated rTmCad1p was conducted per manufacturer recommendation. Purified rTmCad1p was analyzed by SDS-PAGE, and the protein concentration was determined with Coomassie Plus Protein Assay Reagent (Pierce, Rockford, Ill.). Concentration and buffer exchange of rTmCad1p was performed using Centricon centrifugal filters (Millipore, Bedford, Mass.).

Peptide Expression Via *E. Coli* ArcticExpress™ (DE3) Transformation

Additional rTmcad1p protein was expressed. in *E. coli* ArcticExpress™ (DE3). Tmcad1p/pET151-D-TOPO plasmid was transformed into *E. coli* ArcticExpress (DE3) host strain and transformants were selected by Ampicillin resistance. Single colony of *E. coli* host was inoculated in Luria broth containing 0.05 mg/mL of Ampicillin. The culture tube was shaken at 37° C. at rpm. The overnight culture was added into fresh LB media in a ratio of 1:100. Once cell density reached 0.6 to 0.8 O.D. at 600 nm, IPTG of 1 mM was added for induction at 25° C. One liter of *E. coli* was cultured and pelleted by centrifugation. Cell pelleted centrifugation was washed with 20 mM sodium phosphate and 500 mM NaCl at pH of 7.8. Cells were also lysed by sonication in lysis buffer (6 M guanidine hydrochloride, 20 mM sodium phosphate and 500 mM NaCl at pH of 7.8). The supernatant was collected by centrifugation. Two mL of Ni-NTA resin was equilibrated in buffer containing 8M urea and chromatography was conducted by batch elution under hybrid conditions and following the Ni-NTA purifications protocols. A elution fraction containing the peptide was pooled and dialyzed against 10 mM Tris-HCl, 0.01% Triton X-100 and pH of 8.0, with two separate buffer changes. Concentration of rTmcad1p was determined by comparing with standard BSA (1 mg/mL), yielding a concentration of about 1 mg/mL with a volume of 5 mL.

Cry3Aa protoxin used was purified from sporulated cultures of *Bacillus thuringiensis* var. *tenebrionis*. Bacterial cultures were grown for three days at 28° C. Spore-crystal mixtures were collected by centrifugation and washed with 1 M NaCl 0.1% Triton-X-100 and then water. Cry3Aa protoxin was solubilized in 50 mM $Na_2CO_3$ 0.1 M NaCl 0.1% β-mercaptoethanol pH 9.8 and further purified using anion exchange chromatography (AKTA FPLC, GE Healthcare, Uppsala, Sweden). Purified Cry3Aa protoxin was quantified using the Coomassie Protein Assay kit (Pierce) using BSA as standard.

Dot-Blot Assay

Example 1

In dot blot assays, 0.1, 0.5, 1, 2.5, 5, and 10 µg of rTmCad1p obtained from *E. coli* BL21 was spotted and dried on Immobilon-P PVDF membrane (Millipore, Billerica, Mass.). The membrane was blocked with 3% bovine serum albumin in PBS (0.08 M $Na_2HPO_4$, 0.02 M $NaH_2PO_4$, 0.1 M NaCl, pH 7.4) for at least one hour. Incubations with target ligands were done for 2 h in PBS, pH 7.4, 0.1% BSA, 0.1% Tween-20. Blots were washed between each step three times for 5 min in wash buffer (PBS buffer, pH 7.4, 0.2% BSA, 0.1% Tween-20). Blots were incubated with 100 nM Cry3Aa (spore/crystalline toxin preparation from *Bacillus thuringiensis* var. *tenebrionis*) in PBS buffer, pH 7.4, 0.1% BSA, 0.3% Tween-20 followed by 1:5000-diluted rabbit anti-Cry3Aa sera (in wash buffer) and 1:5000-diluted ECL peroxidase-labeled anti-rabbit sera (in wash buffer). ECL Western blotting detection reagent (Amersham RPN2209) was used to visualize peroxidase activity on a Fluor Chem imager (Innotech). All steps were carried out at room temperature on an orbital shaker. rTmCad1p bound Cry3Aa but not BSA, indicating specificity for binding to this peptide (FIG. 1A). Binding was detected with 10 μg of rTmCad1p, but toxin binding to 1 μg peptide was barely detectable.

Toxin Binding in-Gel Assay

Example 2

Toxin binding in-gel assays were according to the manufacturer recommendation (LI-COR Biosciences, Lincoln, Nebr.). Briefly, rTmCad1p obtained from E. coli BL21, was separated by SDS-PAGE on a 10-20% Tricine gel with Tricine sample and running buffers (Invitrogen, Carlsbad, Calif.). After electrophoresis, gels were fixed in 45% methanol/10% acetic acid for 15 min. Separate gels were either stained with Coomassie blue (Imperial Protein Stain, Pierce Chemical Co., Rockford, Ill.), or were incubated with 2.35 μg IR-labeled toxin in 10 mL 1% BSA in 1× wash buffer (0.002 M imidazole-buffered saline with 0.02% Tween 20, KPL, Gaithersburg, Md.), with or without 100-fold excess rTmCad1p, overnight at room temperature with gentle shaking. Gels were washed thrice in wash buffer and scanned at 800 nm on an Odyssey Imager using v. 1.2.15 Odyssey software (LI-COR).

Chymotrypsin-activated Cry3Aa was labeled with a fluorescent dye using the IRDye 800CW Protein Labeling Kit (LI-COR Biosciences, Lincoln, Nebr.). The dye forms a stable ester conjugate with the toxin and has an emission maximum of 789 nm in 1×PBS. IR-labeled toxin was used in toxin-binding assays.

Figure 1B:
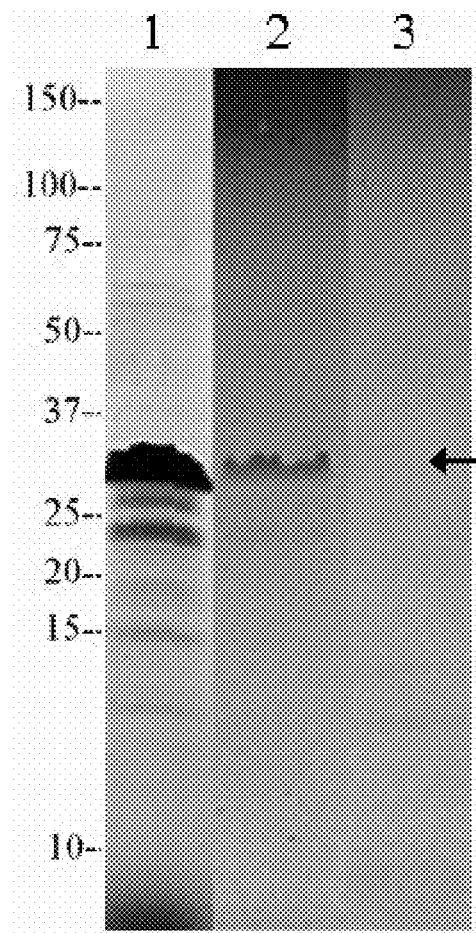
FIG. 1B is a digital image of an in-gel toxin binding competition assay of 5 μg of rTmCad1p and Cry3Aa recognized by a Cry3Aa-antibody with an infrared labeled dye.

The IR-labeled Cry3Aa bound to peptide (FIG. 1B, lane 2), and this binding was completely inhibited by addition of rTmCad1p peptide to the labeled toxin (FIG. 1B, lane 3), suggesting specificity in the peptide/toxin interaction. These results are evidence that Cry3Aa binds specifically to this region of TmCad1.

*Tenebrio Molitor* Larvae Inhibition Bioassays

Figure 3:
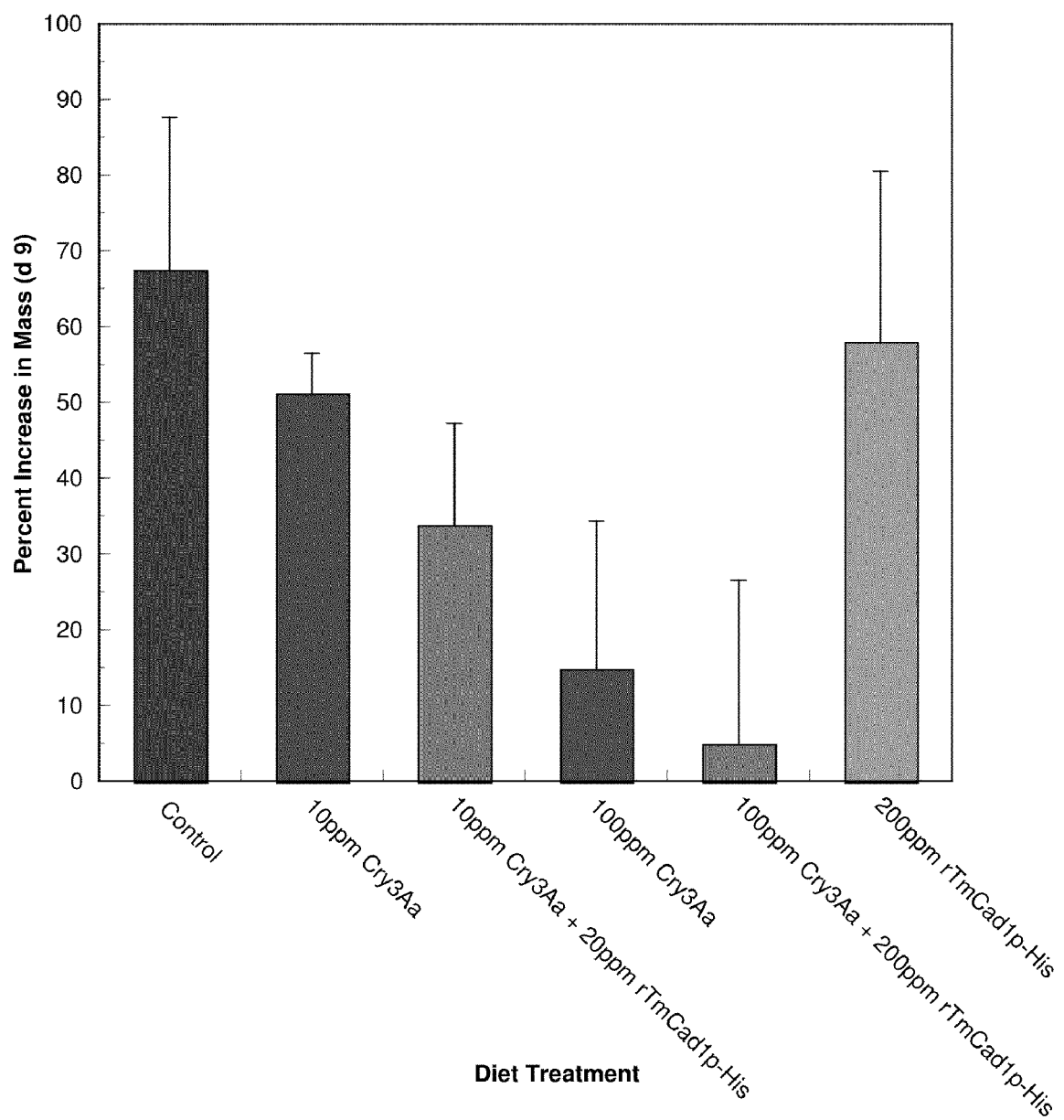
FIG. 3 is a graph of a percentage change of *Tenebrio molitor* larvae weight when subjected to rTmCad1p premixed with Cry3Aa (1:5 molar ratio of Cry3Aa:rTmCad1p) and fed diet at various mass ratios and toxin concentrations as a function of time (days). rTmCad1p was obtained from *E. coli* BL21 transformation.

Example 3 rTmCad1p obtained from E. coli BL21, was premixed with Cry3Aa and added to the diet (10 mg total comprising of 50% glucose/30% yeast/20% wheat germ) with a *T. molitor* larva, as indicated in FIG. 3. rTmCad1p was mixed with 10 ppm (0.154 μM) or 100 ppm (1.54 μM) Cry3Aa to maintain a molar ratio of 1:5 toxin:rTmCad1p. *T. molitor* larvae aged approximately 1 month and weighed 1.4-4.3 mg when placed on diets. Larvae were weighed at regular intervals, and the percent change in the mass±S.D. were determined. Although the difference between treatments and control were not statistically significant (one-way ANOVAs with Holm-Sidak comparisons) because of the large variation in larval weights, larvae fed rTmCad1p were smaller than those without peptide or control.

Figure 4:
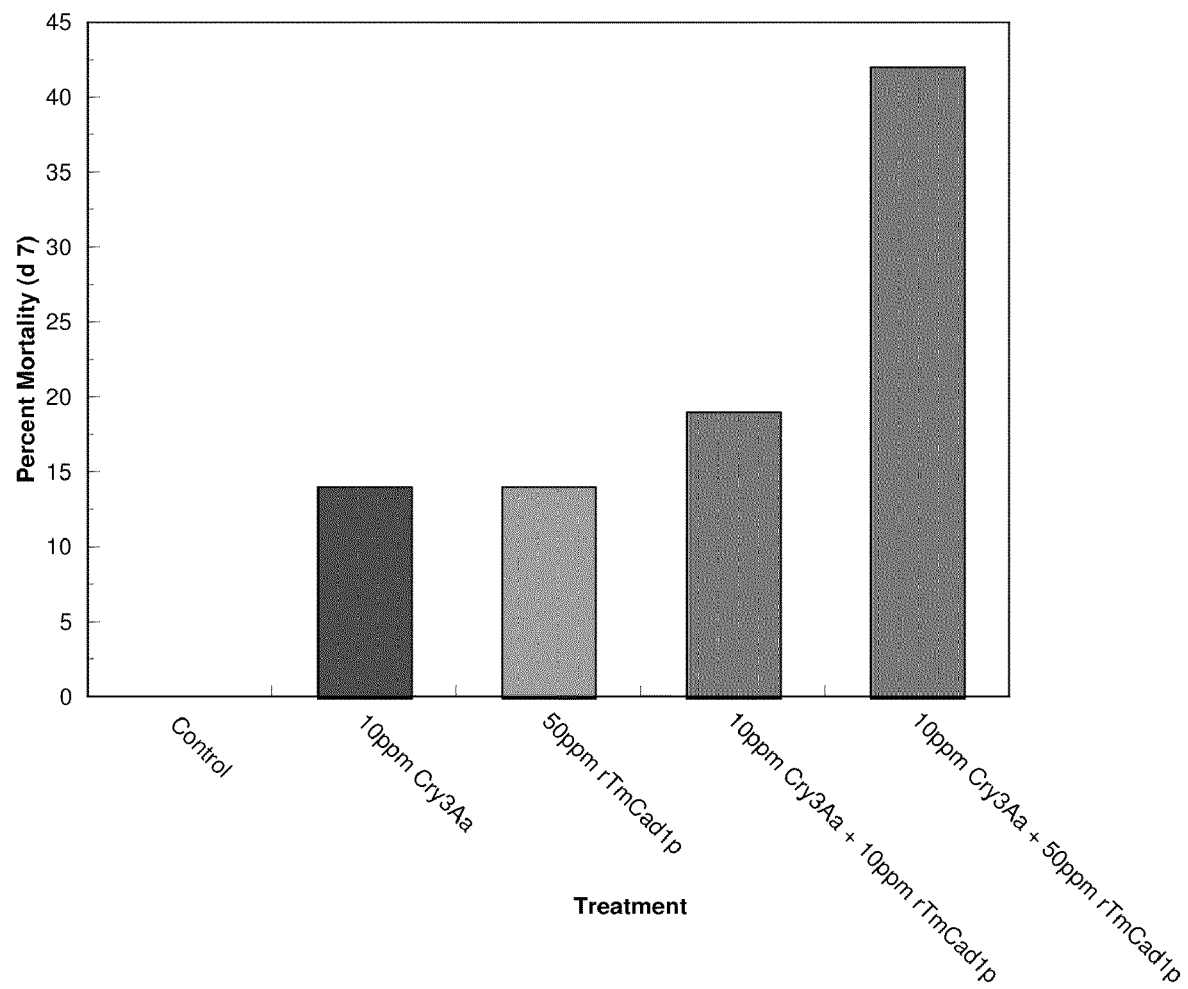
FIG. 4 is a graph of mortality percentage for *Tenebrio molitor* larvae fed a combination of rTmCad1p peptide premixed with Cry3Aa (Cry3Aa: rTmCad1p molar ratios of 1:2.5 and 1:12.4) and whole grain bread diet at various mass ratios on a microtiter plate over a period of one week. rTmCad1p was obtained from *E. coli* BL21 transformation.
Figure 5A:
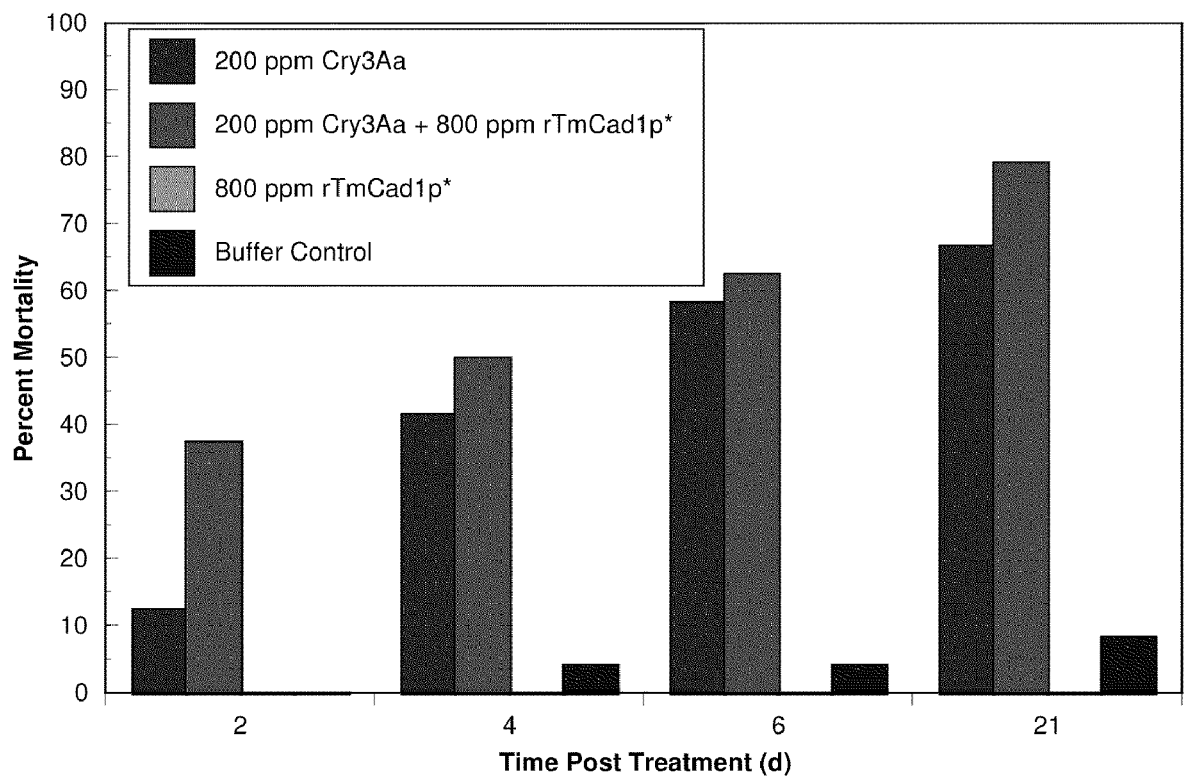
FIGS. 5A, B, and C are graphs of mortality percentage for *Tenebrio molitor* neonate larvae fed in combination of rTmCad1p peptide premixed with Cry3AA at various molar ratios of 1:20 and 1:200 (Cry:rTmCad1p) ratios. Specifically.
Figure 5B:
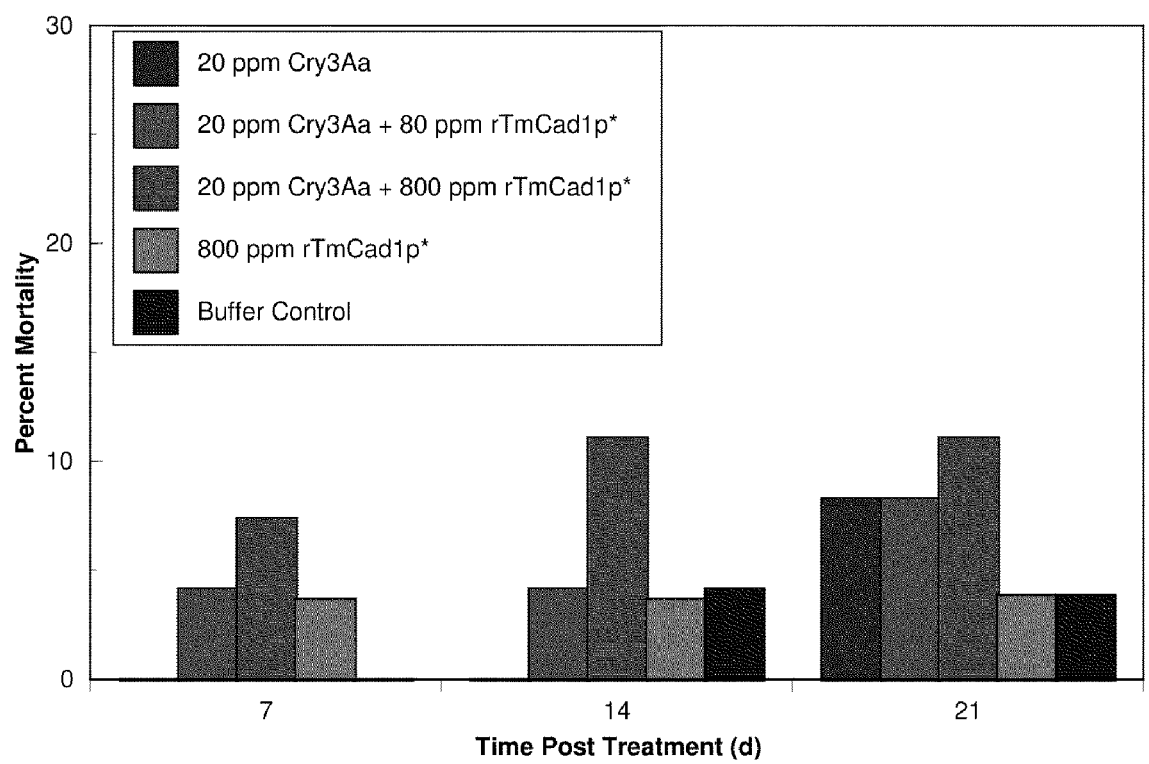
Figure 5C:
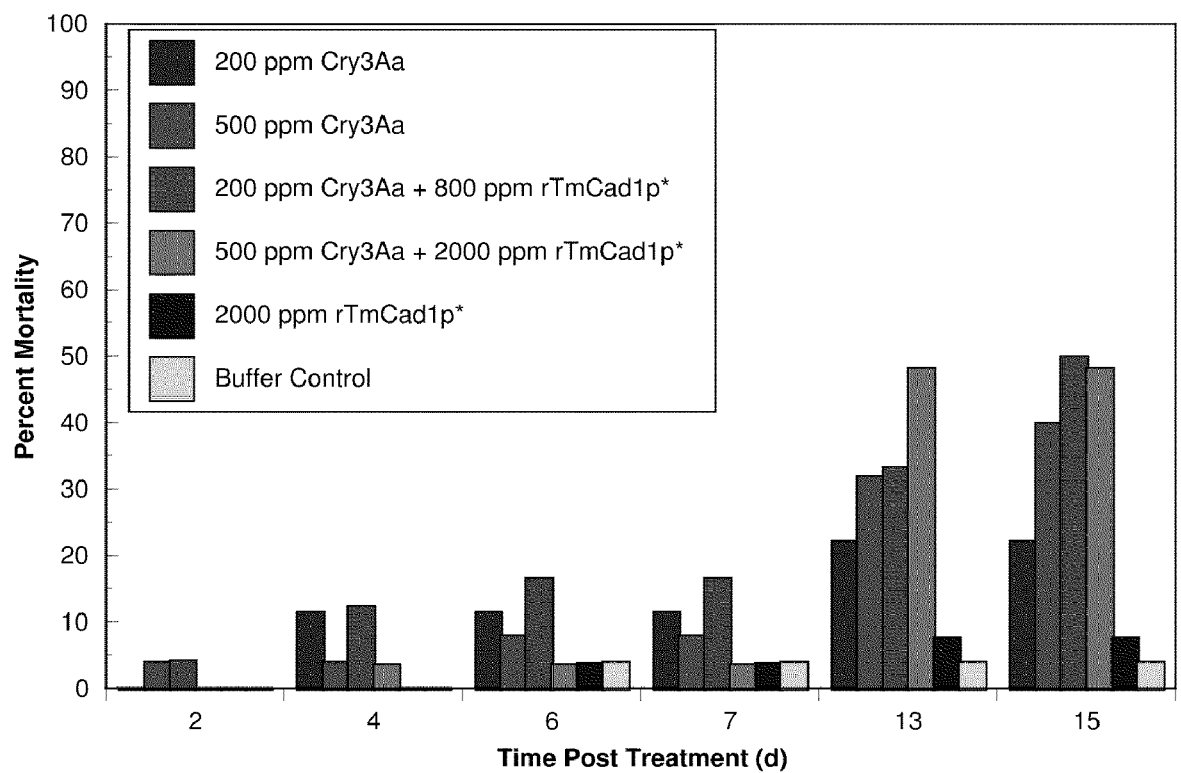

Bioassay results of *T. molitor* using whole grain bread discs cut using a 2 mm cork borer and placed into a microtiter plate well are shown in FIG. 4. Doses of Cry3Aa toxin, rTmCad1p peptide, or toxin and peptide at Cry3Aa:rTmCad1p molar ratios of 1:2.5 and 1:12.4 were added to each bread disc in 5 μl total volume as indicated, and the plate was equilibrated at 25° C., 60% RH., for 24 h. Molar ratios were calculated using molecular weight of Cry3Aa as 65,000 Da and that of rTmCad1p as 26,200 Da. Newly hatched *T. molitor* larvae were added with gentle forceps to each well, and wells were covered with an air-permeable membrane (Breathe-easier, DIVBIO). Mortality was evaluated after 7 days.

rTmCad1p obtained from E. coli ArcticExpress (DE3), was premixed with Cry3Aa and added to the diet (10 mg total comprising of 50% glucose/30% yeast/20% wheat germ) with *T. molitor* larvae as indicated supra. Molar ratios of 1:20 and 1:200 of CryAa:rTmCad1p were evaluated as indicated in FIG. 5A-C. In trial 1, at a molar ratio of 1:20 CryAa: rTmCad1p, had a increase in mortality percentage against solely Cry3Aa. Specifically, as indicated in FIG. 5A, potentiating occurred most following 2 days post treatment with three-fold increase in mortality with respect to 200 ppm of Cry3Aa against 200 ppm Cry3Aa mixed with 800 ppm of rTmCad1p.

Inhibition of Subseptible *Pectinophora Gossypiella* with rTmCad1p and Cry1Ac

Example 4

Larval mortality and weight bioassays were conducted with 40 ppm of rTmCad1p (1.48 μM) was derived from *E. coli* BL21 and was premixed with 1 ppm (7.41 nM) Cry1Ac and added to the diet of *Pectinophora gossypiella* first-instar larva. As indicated in FIG. 7 and FIG. 8 different diet treatments were tested, including control diet with dialysis buffer (0.01 M Tris-HCl, pH 8.0, 0.01% Triton X-100), control diet with TmCad1p, Cry1Ac protoxin-treated diet with dialysis buffer, and Cry1Ac protoxin-treated diet with rTmCad1p. Bioassays show that the combination of Cry1Ac and TmCad1p results in a decrease in weight gained by developing pink bollworm larvae (FIG. 7) compared to the Cry1Ac toxin alone over time. Cry1Ac-susceptible *Pectinophora gossypiella* larvae (APHIS-S or APHIS) were used in bioassays as indicated in FIG. 7 and FIG. 8. Susceptible *Pectinophora gossypiella* is known to be Bt cotton and Cry1Ac (LC50 of approximately 0.25 ug Cry1Ac per mL of artificial diet). The source of Cry1Ac protoxin was produced as a recombinant protoxin in *E. coli*. The molar concentration of Cry1Ac protoxin was determined using 135,000 Da as its molecular weight. *Pectinophora gossypiella* larvae were reared on wheat germ artificial diet as described previously (Bartlett and Wolf, 1985. In R. F. Moore and P. Singh [eds.], Handbook of Insect Rearing, Vol. 2: 415-430. Elsevier Science, Amsterdam).

Inhibition of Resistant *Pectinophora gossypiella* with rTmCad1p and Cry1Ac rTmCad1p obtained from *E. coli* ArcticExpress (DE3), was premixed with Cry1Ac and added to the diet with *Pectinophora gossypiella* larvae as indicated supra, however *Pectinophora gossypiella* larvae used in FIG. 9 is a Cry1Ac resistant strain (AZP-R). The AZP-R resistant stain was provided by the University of Arizona and is published characterizing the resistance (Tabashnik et al., 2004 J. Econ. Ento. 97(3), 721-726.) A bioassay with 30 Cry1Ac-resistant larvae were treated with 1 ppm Cry1Ac inconjuction with 40 ppm rTmCad1p for a molar ratio of 1:200 of Cry1Ac:rTmCad1p as indicated in FIG. 9. After 21 day post initiation, the combination of rTmCad1p mixed with Cry1Ac increased mortality percentage against solely Cry1Ac with and increase of approximately 1.5-fold (19%) in mortality with respect to 1 ppm of Cry1Ac against 1 ppm Cry1Ac mixed with 40 ppm of rTmCad1p.

Inhibition of *Heliothis Virescens* with rTmCad1p and Cry1Ac

Larvae of insects of the genus constitute agricultural pests for major agricultural crops such as tobacco, cotton, soybean.

Figure 10:
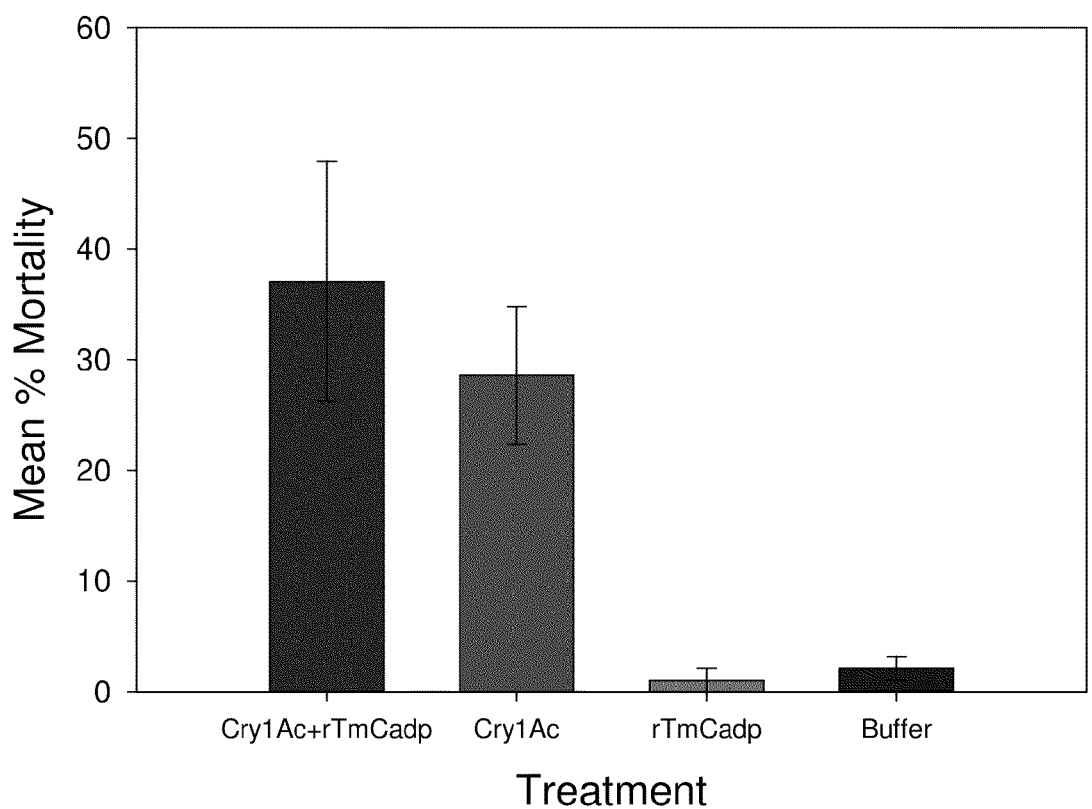
FIG. 10 is a graph of percentages of *Heliothis virescens* larval mortality. Results shown are the means from a bioassay replicated thrice ($n=32$ larvae per treatment per replicate) with *H. virescens* neonates exposed to HD-73 Cry1Ac protoxin and rTmCad1p (expressed from *E. coli* ArcticExpress (DE3)) using 1:200 (toxin:peptide) molar ratio. *H. virescens* eggs were purchased from Benzon Inc. (Carlisle, Pa.). Each column represents data for the mean±standard errors.

A bioassay with *Heliothis virescens* neonates having no known *Bacillus thuringiensis* resistance, were obtained from Benzon Inc. (Carlisle, Pa.). A plurality of treatments (n=3) were conducted against 32 larvae per treatment to determine whether HD-73 Cry1Ac would be potentiate with a mixture of rTmCad1p. Specifically, rTmCad1p obtained from *E. coli* ArcticExpress (DE3) vector was mixed at a 1:200 Cry1Ac to rTmCad1p molar ratio. As detailed in FIG. 10, the mean percentage of mortality of neonates increased with a toxin/peptide combination rather than solely peptide or Cry1Ac toxin. Artificial diet (tobacco budworm diet, Bio-Serv, Frenchtown, N.J.) was prepared following manufacturer's instructions. Approximately 1 mL of diet was poured per well of a bioassay tray (BAW-128, C-D International, Pitman, N.J.) and cooled down at room temperature until diet solidified. Toxin or toxin plus rTmCad1p solutions were diluted in buffer (50 mM $Na_2CO_3$ pH 9.8, 0.3 M NaCl) and 50 µl homogeneously overlayed per well containing solidified artificial diet. Controls included buffer or rTmCad1p alone. After the solutions dried on the diet surface, a single neonate larva of *H. virescens* was placed in each well with a fine brush. Wells were sealed with adhesive plastic lids with small holes to allow gas exchange. Larvae were held at 28° C. with a 16L:8D photoperiod. Larvae were scored for mortality after seven days.

Transient Expression of TmCad1(EC12-Cyto) in Cultured Insect Cells and Cytotoxicity Assays Example 5

Heterologous Expression of TmCad1(EC12-Cyto) in Insect Cell Cultures

To test the receptor function of SEQ. ID. NO: 3, and based on previous identification of Bt toxin functional receptor sites in cadherins (Hua et al., 2004. *Insect Biochem. Mol. Biol.*, 34(3):193-202), nucleotides 3,964-4,879 of SEQ. ID. NO: 3 corresponding to the homologous region to Cry1 functional receptor region in lepidopteran cadherin were cloned. The partial TmCad1 sequence including amino acids 1322-1626 of SEQ. ID. NO: 3 is referred as TmCad1(EC12-cyto) (SEQ. ID. NO.: 28).

For expression of the partial rTmCad1 corresponding to extracellular domain 12 through the end of the cytoplasmic domain (rTmCad1(EC12-cyto)) in insect cell culture, Tm18 and Tm19 were used to PCR amplify cDNA corresponding to nucleotides 3,964-4,878 and subcloned into pCR2.1-TOPO. Using TmCad1(EC12-cyto) cloned in pCR2.1 as template and the PCR supermix (Invitrogen), TmCad1(EC12-cyto) was amplified using PCR primers (Table 2) containing EcoRI (Tm20) or NotI (Tm21) restriction sites at the 5' position. The 938 bp TmCad1(EC12-cyto) PCR amplicon was gel-purified using the S.N.A.P. gel purification kit (Invitrogen) and digested with EcoRI and NotI (Invitrogen) overnight at 37° C. Products were separated by 1% agarose gel electrophoresis, and DNA purified as for PCR amplicons. TmCad1(EC12-cyto) was cloned into pIZT/V5/H is vector predigested with EcoRI and NotI using T4 DNA ligase (Invitrogen) following manufacturer's instructions. Ligation reactions were used to transform chemically competent One Shot cells (Invitrogen) following manufacturer's suggested protocol to obtain pIZT/TmCad1(EC12-cyto). Transformants were selected on LB plates containing 50 µg/mL zeocin. The presence of TmCad1 (EC12-cyto) insert was tested with restriction digestion assays and by DNA sequencing in both directions (UT sequencing facility, Knoxyille, Tenn.).

To target expression of TmCad1 (EC12-cyto) to the cell membrane of insect cells, a fragment corresponding to the signal peptide of *Heliothis virescens* cadherin (HevCaLP) was inserted using engineered KpnI and EcoRI sites. The signal peptide of HevCadLP was cloned using PCR with specific primers (Table 2) containing KpnI (Hv1) or EcoRI (Hv2) restriction sites at the 5' ends. PCR amplicons were purified using the Qiaquick Nucleotide removal kit (Qiagen). After digestion with EcoRI and KpnI, fragments were ligated using T4 ligase into pIZT/TmCad1(EC12-cyto) previously digested with KpnI and EcoRI to obtain the pIZT/Hvseq/TmCad1(EC12-cyto) construct. Ligation reactions were used to transform competent DH5a *E. coli* cells. Clones containing pIZT/Hvseq/TmCad1(EC12-cyto) were selected with zeocin (50 µg/mL) on LB plates. Selected clones were checked with restriction enzymes for correct insert orientation and used for midipreps. Plasmid DNA was purified from midipreps using Qiagen HiSpeed plasmid purification kit following manufacturer's instructions. Purified plasmid was sequenced in both directions at the UT sequencing facility (Knoxyille, Tenn.) to confirm insertion and for correct reading frame.

For transient expression of TmCad1(EC12-cyto) in insect cell cultures, *Trichoplusia ni* Hi5 (Invitrogen) was used. Insect cell cultures were grown in serum-free insect cell media (Hyclone). For lipofection, approximately $1.5 \times 10^6$ cells from a confluent culture were resuspended in 5 mL fresh media and allowed to adhere overnight to 60×15 mm polystyrene dishes (Falcon). Plasmid transfection mixtures were prepared by mixing either 2.5 µg of pIZT/V5/His or 5 µg of pIZT/Hvseq/TmCad1(EC12-cyto) plasmid with 1 mL of serum-free insect medium (Hyclone) and 20 µl of Cellfectin reagent (Invitrogen). Cells were incubated for four hours with the transfection mixture and then changed to fresh media and incubated at 26° C. for 2 days.

Figure 6A:
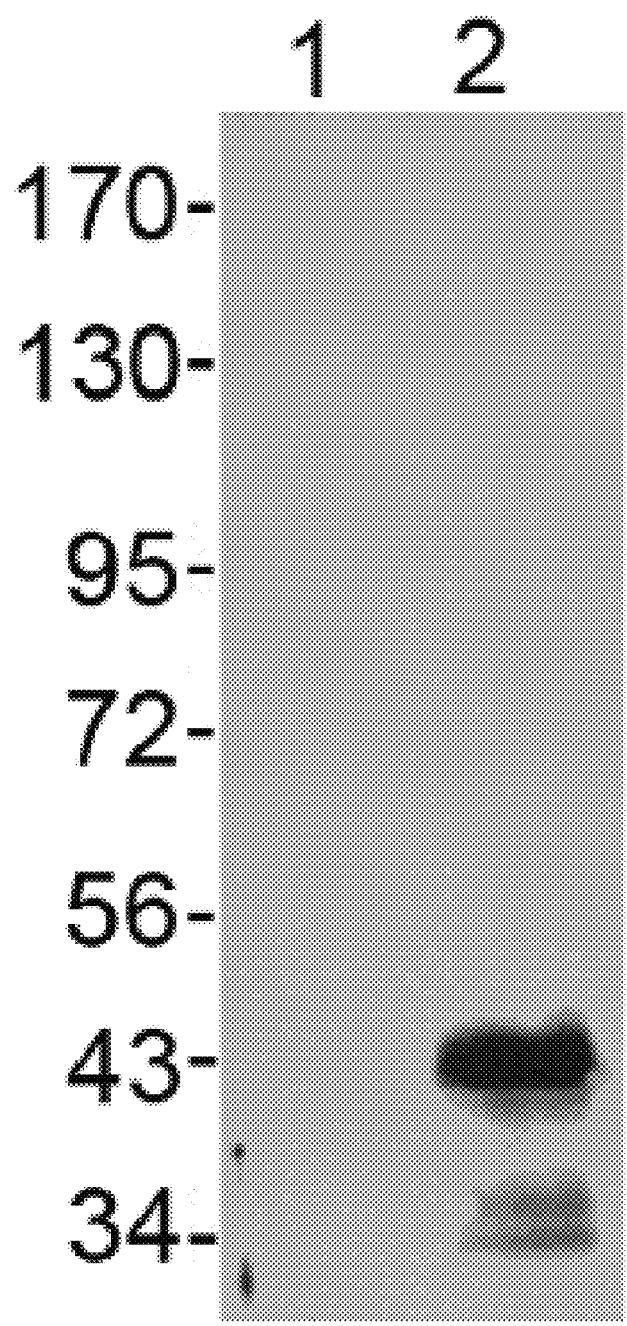
FIG. 6A is digital image of immunoblot showing detection of expression of TmCad1(EC12-cyto) in Hi5 insect cells (Invitrogen) transfected with pIZT/TmCad1(EC-12-cyto) (lane 2) in comparison to Hi5 cells transfected with mock plasmid pIZT (lane 1).

Immunoblotting with rTmCad1p antisera was used to test for TmCad1(EC12-cyto) expression (FIG. 6A). Approximately $1 \times 10^6$ cells were pelleted by centrifugation at 14,500×g for 2 min. and then washed twice with 1 mL of PBS buffer (135 mM NaCl, 2 mM KCl, 10 mM $Na_2HPO_4$, 1.7 mM $KH_2PO_4$, pH 7.5). Final pellets were solubilized in 50 µl of SDS-PAGE buffer and separated in 8% SDS-PAGE electrophoresis. Proteins were transferred to PVDF filters and filters blocked with PBS plus 1% Tween-20 (PBST) plus 3% BSA. Blots were probed sequentially with 1:5,000 dilution of rTmCad1p antisera and 1:20,000 dilution of goat anti-rabbit-HRP conjugate. Cross-reacting proteins were detected using enhanced chemiluminescence substrates (Western pico, Pierce). pIZT/Hvseq/TmCad1 (EC12-cyto)-transfected *T. ni* Hi5 cells expressed on their membrane a protein of about 44 kDa, the predicted size for TmCad1(EC12-cyto) plus tags, that cross-reacted with rTmcad1p antisera (FIG. 6A).

To test the functional receptor function of TmCad1(EC12-cyto), cytotoxicity assays were performed via fluorescent microscopy and flow cytometry assays. Briefly, insect cells were transfected and incubated for a period of 2 days, followed by a media change and transfer of cells to a 12-well tissue culture plate (Falcon). Upon incubation at 26° C. overnight, 50lβ/mL for S2 cells or 10 µg/mL for Hi5 cells of Cry3Aa protoxin (approximately 800 nM and 160 nM protoxin concentration, respectively) was added and the cells incubated at 26° C. for four hours. Cells were stained with 1 µg/mL of propidium iodide (PI) for 5 min, then immediately observed for GPF fluorescence (green fluorescent protein) and PI (propidium iodide) staining using a flow cytometer (LSR benchtop flow cytometer, Beckton Dickinson, USA). To calculate the percentage of GFP positive cells in the pIZT/Hv/TmCad1(EC12-cyto) cell population killed by Cry3A toxins (FIG. 6B), the formula in Table 3 was utilized. The formula accounts for the dead cells (PI-positive) in an untreated population, GFP positive dead cells that lost GFP due to cell leakage, and the observed transfection efficiency.

TABLE 3

$$= \left[ \frac{(GFP^+PI^+Cells_{Toxin} + GFP^-PI^+Cells_{Toxin}) - \frac{(GFP^+PI^+Cells_{control} + GFP^-PI^+Cells_{control})}{GFP^+Cells_{Toxin}}}{} \right] \times 100$$

Figure 6B:
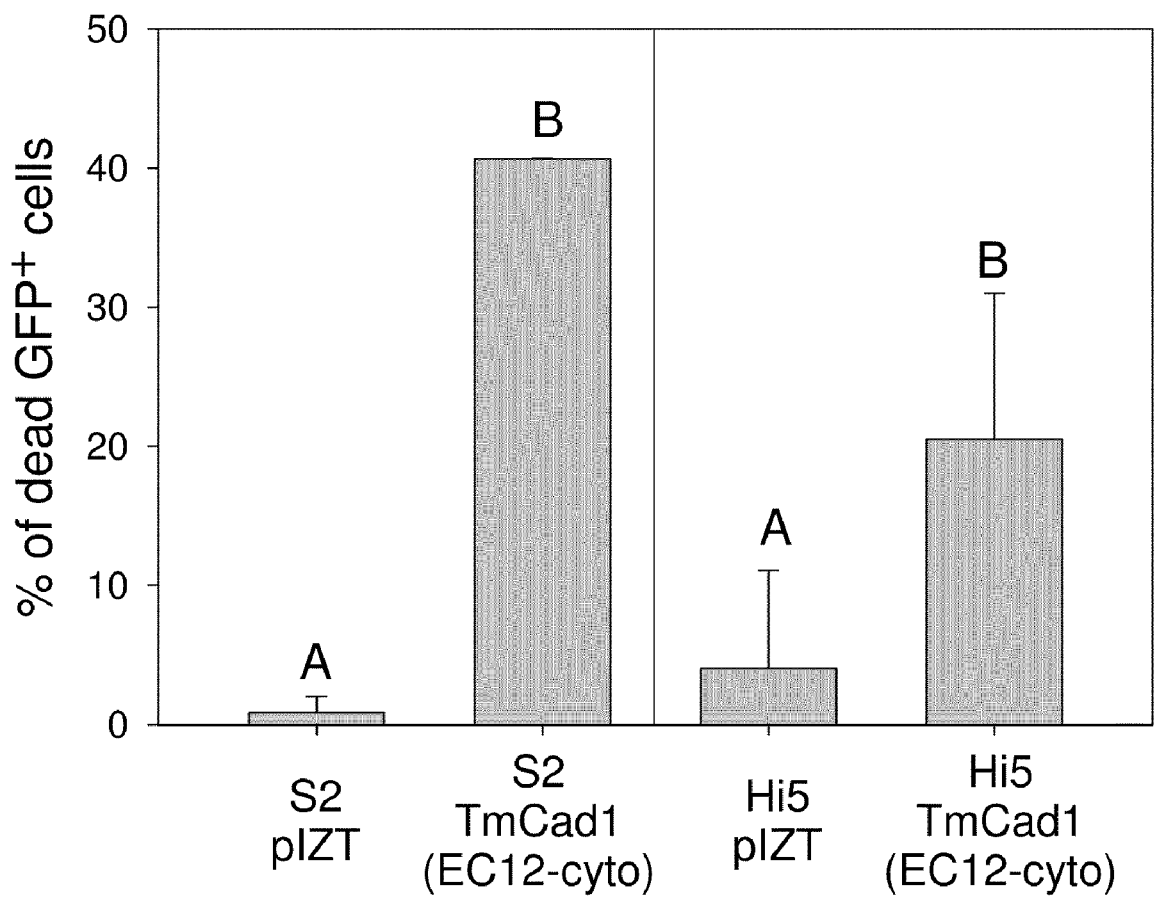
FIG. 6B is a graph of mortality of S2 or Hi5 cells transfected with pIZT or pIZT/TmCad1(EC12-cyto) when exposed to approximately 800 nM (S2 cells) or 110 nM (Hi5 cells) of Cry3Aa protoxin. Significant statistical differences between control and experimental cells based on Student's t-test ($P<0.09$, $n=3$) are denoted as different letters.
Figure 7:
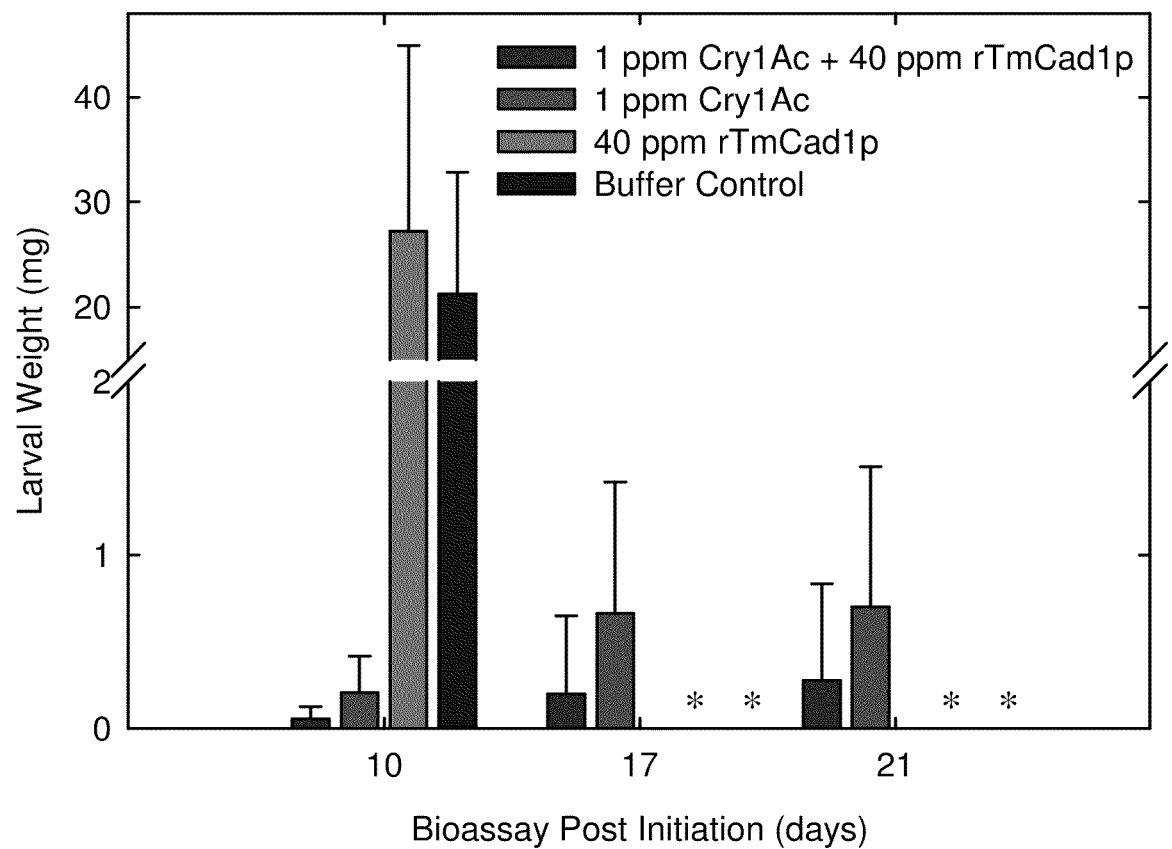
FIG. 7 is a graph of a percentage change of *Pectinophora gossypiella* (APHIS) larvae weight when subjected to combination of a control diet, dialysis buffer, and rTmCad1p premixed with Cry1Ac in a 1:200 molar ratio to toxin:peptide as a function of time (days). Said *Pectinophora gossypiella* (APHIS) larvae are known to be subseptible to Cry1Ac.
Figure 8:
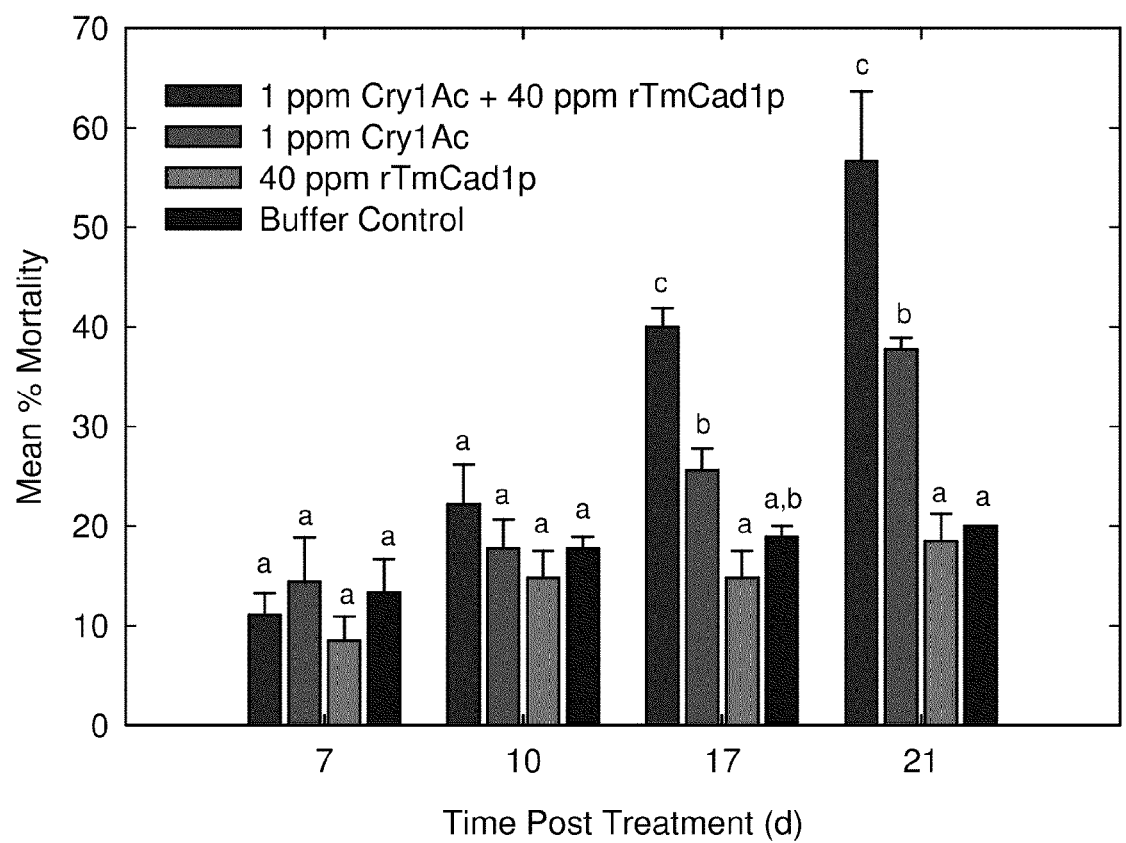
FIG. 8 is a graph of morality percentages of *Pectinophora gossypiella* (AZP-R) larvae fed a combination of a control diet, dialysis buffer, and rTmCad1p premixed with Cry1Ac in a 1:200 molar ratio to toxin:peptide as a function of time (days). Said *Pectinophora gossypiella* (AZP-R) larvae are known to be resistant to Cry1 Ac.

As shown in FIG. 6B, Cry3Aa treatment induced 40% and almost 25% cytotoxicity in S2 and Hi5 cells expressing TmCad1(EC12-cyto), respectively and provides evidence for the functional role of this peptide as Cry3Aa receptor.

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. An insecticide composition comprising an effective amount of cadherin peptide comprising SEQ. ID. NO: 2 and an effective amount of *Bacillus thuringiensis* Cry protein.

2. The insecticide composition of claim 1 wherein the cadherin peptide and *Bacillus thuringiensis* Cry protein is in a molar ratio range of approximately 1:2.5 to 1:200.

3. An insecticide composition comprising an effective amount of a cadherin peptide comprising SEQ. ID. NO:2 and an effective amount of *Bacillus thuringiensis* Cry protein, wherein the Cry protein is a Cry1 or Cry3 protein.

4. The insecticide composition of claim 3 wherein the composition is effective against insects of the order Coleoptera.

5. The insecticide composition of claim 4 wherein the composition is effective against *Tenebrio molitor*.

6. The insecticide composition of claim 3 wherein the composition is effective against insects of the order Lepidoptera.

7. The insecticide composition of claim 6 wherein the composition is effective against *Pectinophora gossypiella*.

8. The insecticide composition of claim 6 wherein the composition is effective against *Heliothis virescens*.

9. The insecticide composition of claim 3 wherein the Cry protein is a Cry3Aa protein and the cadherin peptide and Cry3Aa protein are in a molar ratio range of approximately 1:20 to 1:200.

10. The insecticide composition of claim 3 wherein the Cry protein is a Cry1Ac protein and the cadherin peptide and Cry1Ac protein are in a molar ratio of approximately 1:200.

* * * * *